United States Patent
Schneider et al.

(10) Patent No.: US 10,689,677 B2
(45) Date of Patent: Jun. 23, 2020

(54) **METHOD FOR THE FERMENTATIVE PRODUCTION OF L-LYSINE BY MODIFIED *CORYNEBACTERIUM GLUTAMICUM***

(71) Applicant: Evonik Operations GmbH, Essen (DE)

(72) Inventors: Frank Schneider, Halle (DE); Georg Thierbach, Bielefeld (DE); Thomas Bekel, Halle (DE); Kornelia Voβ, Steinhagen (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/574,588

(22) Filed: Sep. 18, 2019

(65) Prior Publication Data

US 2020/0095622 A1 Mar. 26, 2020

(30) Foreign Application Priority Data

Sep. 26, 2018 (EP) .................................... 18196725

(51) Int. Cl.
*C12P 13/08* (2006.01)

(52) U.S. Cl.
CPC .................................... *C12P 13/08* (2013.01)

(58) Field of Classification Search
None
See application file for complete search history.

(56) References Cited

U.S. PATENT DOCUMENTS

| | | | |
|---|---|---|---|
| 4,656,135 | A | 4/1987 | Tsuchida et al. |
| 5,275,940 | A | 1/1994 | Kino et al. |
| 5,279,744 | A | 1/1994 | Itoh et al. |
| 5,431,933 | A | 7/1995 | Binder et al. |
| 5,688,671 | A | 11/1997 | Sugimoto et al. |
| 5,763,230 | A | 6/1998 | De Hollander et al. |
| 5,770,409 | A | 6/1998 | Pfefferle et al. |
| 5,990,350 | A | 11/1999 | Stevens et al. |
| 6,025,169 | A | 2/2000 | Nakamura et al. |
| 6,420,151 | B1 | 7/2002 | Eikmanns et al. |
| 6,670,156 | B1 | 12/2003 | Moeckel et al. |
| 6,844,176 | B1 | 1/2005 | Bathe et al. |
| 6,858,406 | B1 | 2/2005 | Vrlijc et al. |
| 6,893,848 | B1 | 5/2005 | Yokoi et al. |
| 7,267,967 | B1 | 9/2007 | Eikmanns et al. |
| 7,332,309 | B2 | 2/2008 | Rieping |
| 7,338,790 | B2 * | 3/2008 | Thierbach ............ C12N 9/0006 435/106 |
| 8,637,295 | B1 | 1/2014 | Claes et al. |
| 8,697,850 | B2 | 4/2014 | Jessberger et al. |
| 8,912,313 | B2 | 12/2014 | Reth et al. |
| 9,422,568 | B2 | 8/2016 | Jessberger et al. |
| 10,533,200 | B2 | 1/2020 | Voss et al. |
| 10,533,718 | B2 | 1/2020 | Voss et al. |
| 2002/0119537 | A1 | 8/2002 | Moeckel et al. |
| 2004/0115816 | A1 | 6/2004 | Pompejus et al. |
| 2004/0171160 | A1 | 9/2004 | Pompejus et al. |
| 2005/0196848 | A1 | 9/2005 | Dusch et al. |
| 2009/0311758 | A1 | 12/2009 | Jessberger et al. |
| 2009/0325244 | A1 | 12/2009 | Herold et al. |
| 2010/0240131 | A1 | 9/2010 | Pompejus et al. |
| 2017/0051324 | A1 | 2/2017 | Ochrombel et al. |
| 2017/0145452 | A1 | 5/2017 | Lee et al. |
| 2017/0204439 | A1 | 7/2017 | Lee et al. |
| 2018/0363014 | A1 | 12/2018 | Voss et al. |
| 2019/0085340 | A1 | 3/2019 | Thierbach et al. |
| 2019/0106721 | A1 | 4/2019 | Bekel et al. |
| 2019/0185890 | A1 | 6/2019 | Voss et al. |

FOREIGN PATENT DOCUMENTS

| | | |
|---|---|---|
| EP | 0 197 335 | 10/1986 |
| EP | 0 219 027 | 4/1987 |
| EP | 0 387 527 | 9/1990 |
| EP | 0 358 940 | 9/1995 |
| EP | 0 811 682 | 12/1997 |
| EP | 0 841 395 | 5/1998 |
| EP | 1 094 111 | 4/2001 |
| EP | 1 096 013 | 5/2001 |
| EP | 1 108 790 | 6/2001 |
| EP | 1 239 040 | 9/2002 |
| EP | 1108790 | * 9/2009 |
| EP | 2 107 128 | 10/2009 |
| EP | 2 796 555 | 10/2014 |
| EP | 2 940 039 | 11/2015 |
| EP | 3 141 597 | 3/2017 |
| EP | 3 144 383 | 3/2017 |

(Continued)

OTHER PUBLICATIONS

Bornscheuer et al. Curr Protoc Protein Sci. Nov. 2011;Chapter 26:Unit26.7. (Year: 2011).*
Accession AAG92962. Jun. 15, 2007 (Year: 2007).*
Accession Q8NLM4. Oct. 1, 2002 (Year: 2002).*
Accession AAH68534. Sep. 26, 2001 (Year: 2001).*
Search Report dated Feb. 14, 2020 in European Application No. 19197646.3.
Do Carmo Félix et al, Critical Reviews in Biotechnology; 2019, 39(8):1031-1055.
European Search Report dated Apr. 25, 2019 in European Application 18196725.8.
Cheng et al., "*Expanding lysine industry: industrial biomanufacturing of lysine and its derivatives,*", Journal of Industrial Microbiology & Biotechnology (2018) 45:719-734, doi: 10.1007/s10295-018-2030-8, XP36562616A.

(Continued)

*Primary Examiner* — Christian L Fronda
(74) *Attorney, Agent, or Firm* — Grüneberg and Myers PLLC

(57) ABSTRACT

A method is used for the fermentative production of L-lysine using bacteria of the species *Corynebacterium glutamicum*, having the ability to excrete L-lysine and containing in their chromosome a mutated NCgl2816 polynucleotide. Further, the method is used for cultivating the bacteria in a suitable medium under suitable conditions, and accumulating said L-lysine in the suitable medium to form an L-lysine containing fermentation broth.

11 Claims, No Drawings

Specification includes a Sequence Listing.

(56) References Cited

FOREIGN PATENT DOCUMENTS

| WO | 97/23597 | 7/1997 |
| WO | 99/18228 | 4/1999 |
| WO | 01/00804 | 1/2001 |
| WO | 02/080685 | 9/2002 |
| WO | 03/014362 | 2/2003 |
| WO | 2008/033001 | 3/2008 |
| WO | 2009/141330 | 11/2009 |
| WO | 2013/000827 | 1/2013 |

OTHER PUBLICATIONS

Meseta Ikeda, "*Lysine Fermentation—History arid Genome Breeding*," Shinshu University, Nagano, 399-4598, Japan, University document, 2017, 54 pages, XP-002790498. Retrieved from the Internet [retrieved on Apr. 10, 2019]: URL:https://core.ac.uk/download/pdf/160827_891.pdf.

Kell et al., "*Membrane transporter engineering in industrial biotechnology and whole cell biocatalysis*," Trends in Biotechnology, Apr. 2015, vol. 33, No. 4, pp. 237-246, doi: 10.1016/j.tibtech.2015.02.001, XP29213203A.

Liu et al,"*Overexpression of genes related to glucose transport system in Corynebacterium glutamicum ZL-8 and their effects on glucose metabolism and L-lysine synthesis*," Food and Fermentation Industries, 2017 vol. 43, No. 7, pp. 27-34, XP-002790499, DOI: 10.13995/j.cnki.11-1802/ts.013796.

Park et al., "*RNA-guided single/double gene repressions in Corynebacterium glutamicum using an efficient CRISPR interference and its application to industrial strain*," Microb Cell Fact (2018) 17:4, pp. 1-10 doi: 10.1186/s12934-017-0843-1, XP55570091A.

Sanchez et al., "*Our microbes not only produce antibiotics, they also overproduce amino acids*," The Journal of Antibiotics (2018) 71, 26-36, XP-002790497, doi:10.1038/ja.2017.142.

Su et al., "*Improved ssDNA recombineering for rapid and efficient pathway engineering in Corynebacterium glutamicum*,", J Chem Technol Biotechnol 2018; 93: 3535-3542, XP-002790496, DOI: 10.1002/jctb.5726.

Viswanath et al., "*Enhancing the Activity of Aspartate Kinase for an Overproduction of L-lysine by Corynebacterium glutamicum*," Am. J. Biochem. Mol. Biol., 6(2): 33-44, 2016. XP-002790530 DOI: 10.3923/ajbmb.2016.33.44.

Yang et al., "*Comparative analysis of Corynebacterium glutamicum genomes: a new perspective for the industrial production of amino acids*," The Author(s) BMC Genomics 2017, 18(Suppl 1): 940, pp. 1-13 DOI: 10.1186/s12864-016-3255-4, XP21238114A.

European Search Report and Opinion completed Oct. 18, 2017 in European Application No. 17 19 1616.

European Search Report issued for corresponding application EP 18 19 4968 completed Nov. 7, 2018.

Blombach et al., Applied and Environmental Microbiology, 2009, 75(2):419-427.

Ikeda et al., Applied Microbiology and Biotechnology, 2003, 62(2-3) :99-109.

Jager et al., Journal of Bacteriology, 1997, 179(7) :2449-2451.

Larkin et al., Bioinformatics, 2007, 23(21):2947-2948.

Lv et al., Journal of Bacteriology, 2012, 194(3):742-743.

Peters-Wendisch et al., Microbiology, 1998, 144(4):915-927.

Schäfer et al., Gene, 1994, 145(1):69-73.

Schwarzer et al., Bio/Technology, 1991, 9:84-87.

Tang et al., Nucleic Acids Research, 1994, 22(14):2857-2858.

Tosaka et al., Agriculture and Biological Chemistry, 1978, 42(2):745-752.

Wendisch et al., World J Microbial Biotechnol, 2016 32: 105: 1-10.

Yukawa et al., Microbiology, 2007, 153(4): 1042-1058.

GenBank Accession No. AGQQ02000001; locus tag KIQ_ 001800; protein ID KE124322; submitted Aug. 31, 2011.

GenBank Accession No. ANU34683; submitted Dec. 11, 2015.

GenBank Accession No. AP009044, nts 2959048-2960427; protein ID BAF55689; submitted Aug. 10, 2005.

GenBank Accession No. AP009044; sequence ID BAF55440; submitted Aug. 10, 2005.

GenBank Accession No. AX066329; protein ID CAC26403 from WO 01/00804 filed Jan. 4, 2001.

GenBank Accession No. BAF55440; submitted Aug. 10, 2005.

GenBank Accession No. BAF55689; submitted Aug. 10, 2005.

GenBank Accession No. BAV24403; submitted Jun. 10, 2016.

GenBank Accession No. CP016335; locus tag BBD29_13545; submitted Dec. 11, 2015.

GenBank Accession No. NC_003450; protein ID NP601971; gene ID 1020721; submitted Sep. 23, 2002.

NCBI Reference Sequence: NP_601971; submitted May 24, 2002.

NCBI Reference Sequence: NZ_ CPO 16335; locus tag BBD29_13545; protein ID WP060565255; submitted Dec. 11, 2015.

GenBank Accession No. U43535; protein ID AAB51443; submitted Dec. 18, 1995.

Extended European Search Report dated Jan. 12, 2017 in European Application No. 17194981.1, 7 pages.

Bennet, Simon, Pharmacogenomics; 2004, 5(4):433-438.

Duetz, Wouter A., TRENDS in Microbiology; 2007, 15(10):469-475.

Eggeling et al., Appl Microbiol Biotechnol; 2015, 99:3387-3394 DOI 10.1007/s00253-015-6508-2.

Eikmanns et al., Microbiology; 1994, 140:1817-1828.

Follettie et al., Journal of Bacteriology; 1993, 175(13): 4096-4103.

Gibson et al., Science; 2008, 319:1215-1220.

Hadiati et al., Bioresources and Bioprocessing; 2014, 1:25.

Keilhauer et al., Journal of Bacteriology; 1993, 175(17):5595-5603.

Kim et al, Mol. Cells; 2001, 12(1):112-116.

Liebl et al., International Journal of Systematic Bacteriology; 1991, 14(2) 255-260.

Lindroth et al., Analytical Chemistry; 1979, 51(11):1667-1674.

McBride, et al., Tetrahedron Letters; 1983, 24(3):245-248.

Peters-Wendisch et al., J. Mol. Microbiol. Biotechnol.; 2001, 3(2):295-300.

Michael V. Pickering, Science; 1989, 7(6):484-487.

Sanger et al., Proc. Natl. Acad. Sci. USA; 1977, (74)12:5463-5467.

Schäfer et al., Journal of Bacteriology; 1990, 172(3):1663-1666.

Simon et al., Bio/Technology; 1983, 1:784-791.

Spackman et al., Analytical Chemistry; 1958, 30(7):1190-1206.

Swenson et al., Manual of Clinical Microbiology; 1995, 13:1356-1367.

Van der Rest et al., Appl Microbiol Biotechnol; 1999, 52:41-545.

GenBank Accession No. KE124322, submitted Aug. 31, 2011.

* cited by examiner

SEQUENCE LISTING

```
<160> NUMBER OF SEQ ID NOS: 8

<210> SEQ ID NO 1
<211> LENGTH: 2001
<212> TYPE: DNA
<213> ORGANISM: Corynebacterium glutamicum ATCC13032
<220> FEATURE:
<221> NAME/KEY: misc_feature
<222> LOCATION: (221)..(221)
<223> OTHER INFORMATION: position 221
<220> FEATURE:
<221> NAME/KEY: CDS
<222> LOCATION: (343)..(1641)
<223> OTHER INFORMATION: coding sequence of NCgl2816
<220> FEATURE:
<221> NAME/KEY: misc_feature
<222> LOCATION: (1000)..(1002)
<223> OTHER INFORMATION: ttc codon for phenylalanine
<220> FEATURE:
<221> NAME/KEY: misc_feature
<222> LOCATION: (1001)..(1001)
<223> OTHER INFORMATION: nucleobase thymine
<220> FEATURE:
<221> NAME/KEY: misc_feature
<222> LOCATION: (1642)..(1644)
<223> OTHER INFORMATION: taa stop codon

<400> SEQUENCE: 1
gccaccaggg attgggccgt acgattcaac gctctcatgg ccattcacgg tcacctacat    60
attcctgccg aaacccgcgt tgatggggta agccacgtgg aggtttcttt gggttacccc   120
tttgaaaaac acccacctca catgaagcgt ccgtggccgt ttccggtcat gcagattaac   180
taactctgtt gcttaaatgg gggtaattgg attcgactgt tttccacacc ccattgacaa   240
ttaaaggtga cacgccttac attcttgtgg tctgaccatg aggttgggcc aatcggtttc   300
agcccgttta ctcccgccgt ccgtttcaga gaagaggtca cc atg aca acc gca     354
                                              Met Thr Thr Ala
                                              1
```

-continued

| | | |
|---|---|---|
| gta gat caa aac tca ccg ccc aag cag caa ctc aac aag cgc gtc ctg<br>Val Asp Gln Asn Ser Pro Pro Lys Gln Gln Leu Asn Lys Arg Val Leu<br>5                                10                        15                    20 | | 402 |
| ctg ggc agc ttg agt ggc agc gtt atc gaa tgg ttc gac ttc ctg gtt<br>Leu Gly Ser Leu Ser Gly Ser Val Ile Glu Trp Phe Asp Phe Leu Val<br>                        25                        30                        35 | | 450 |
| tac gga acc gtc gcc gcg ctg gtc ttc aac aag atg tac ttc ccc agc<br>Tyr Gly Thr Val Ala Ala Leu Val Phe Asn Lys Met Tyr Phe Pro Ser<br>                    40                        45                      50 | | 498 |
| ggc aac gag ttc ctc tcc aca atc ctg gcg tac gca tcc ttc tcc ctg<br>Gly Asn Glu Phe Leu Ser Thr Ile Leu Ala Tyr Ala Ser Phe Ser Leu<br>        55                        60                        65 | | 546 |
| acc ttc ttc ttc cgc ccc att ggt ggc gtc atc ttc gcc cac atc ggc<br>Thr Phe Phe Phe Arg Pro Ile Gly Gly Val Ile Phe Ala His Ile Gly<br>70                                75                        80 | | 594 |
| gac cgc att ggg cgt aag aag acc ctg ttc atc acc ttg atg ctc atg<br>Asp Arg Ile Gly Arg Lys Lys Thr Leu Phe Ile Thr Leu Met Leu Met<br>85                                90                        95                    100 | | 642 |
| ggt ggc ggc acc gtc gcc att ggt ttg ctg ccc gac tac aac gcc atc<br>Gly Gly Gly Thr Val Ala Ile Gly Leu Leu Pro Asp Tyr Asn Ala Ile<br>                        105                       110                     115 | | 690 |
| ggc att tgg gca cca atc ctt ctg atg ttc ctc cgc att ttg cag ggc<br>Gly Ile Trp Ala Pro Ile Leu Leu Met Phe Leu Arg Ile Leu Gln Gly<br>                  120                       125                     130 | | 738 |
| atc gga att ggc ggc gaa tgg ggt ggc gca ctc ctg gca tac gaa<br>Ile Gly Ile Gly Gly Glu Trp Gly Gly Ala Leu Leu Leu Ala Tyr Glu<br>           135                       140                     145 | | 786 |
| tac gct cca aag aag cag cgt ggg ctc tac ggc gca gtt cct caa atg<br>Tyr Ala Pro Lys Lys Gln Arg Gly Leu Tyr Gly Ala Val Pro Gln Met<br>150                            155                        160 | | 834 |
| ggc att tcc ctg ggc atg ctg ctt gca gct ggc gtg atc tct ctg ctc<br>Gly Ile Ser Leu Gly Met Leu Leu Ala Ala Gly Val Ile Ser Leu Leu<br>165                            170                        175                    180 | | 882 |
| acc ctc atg ccg gaa gat cag ttc ctc acc tgg ggc tgg cgc atc cca<br>Thr Leu Met Pro Glu Asp Gln Phe Leu Thr Trp Gly Trp Arg Ile Pro<br>                  185                       190                     195 | | 930 |
| ttc gtc gga tcc atc ctc cta gtg ttc atc ggc ctg ttc atc cga aac<br>Phe Val Gly Ser Ile Leu Leu Val Phe Ile Gly Leu Phe Ile Arg Asn<br>                200                       205                     210 | | 978 |
| ggc ctt gat gaa acc ccc gag ttc aag cgt atc cgc gat tcc ggc cag<br>Gly Leu Asp Glu Thr Pro Glu Phe Lys Arg Ile Arg Asp Ser Gly Gln<br>         215                       220                     225 | | 1026 |
| cag gta aag atg cct ctg aag gaa gtt ctg acc aag tac tgg cca gcc<br>Gln Val Lys Met Pro Leu Lys Glu Val Leu Thr Lys Tyr Trp Pro Ala<br>230                          235                        240 | | 1074 |
| gtt ctg gtc tcc atc ggc gca aaa gct gcc gag acc ggc ccc ttc tac<br>Val Leu Val Ser Ile Gly Ala Lys Ala Ala Glu Thr Gly Pro Phe Tyr<br>245                          250                        255                    260 | | 1122 |
| atc ttc ggc acc tac atc gtt gct tac gca acc aac ttc ctg aac atc<br>Ile Phe Gly Thr Tyr Ile Val Ala Tyr Ala Thr Asn Phe Leu Asn Ile<br>                  265                       270                     275 | | 1170 |
| cgc gac aac att gtc ctt ctg gca gtt gct tgc gcc gcc ctc gtt gcc<br>Arg Asp Asn Ile Val Leu Leu Ala Val Ala Cys Ala Ala Leu Val Ala<br>                    280                       285                     290 | | 1218 |
| acc atc tgg atg cca ctg ttc gga tcc ttc tcc gac cgc gtc aac cgt<br>Thr Ile Trp Met Pro Leu Phe Gly Ser Phe Ser Asp Arg Val Asn Arg<br>              295                       300                     305 | | 1266 |
| gca gtg ctc tac agg atc tgt gca tcc gca acc atc gtg ctg att gtc<br>Ala Val Leu Tyr Arg Ile Cys Ala Ser Ala Thr Ile Val Leu Ile Val<br>310                          315                        320 | | 1314 |

```
cct tac tac ttg gtc ctc aac acc ggc gaa att tgg gca ctg ttt atc      1362
Pro Tyr Tyr Leu Val Leu Asn Thr Gly Glu Ile Trp Ala Leu Phe Ile
325                 330                 335                 340 act acc gtg att ggc ttc ggc atc ctc tgg ggt agc gtc aac gca atc      1410
Thr Thr Val Ile Gly Phe Gly Ile Leu Trp Gly Ser Val Asn Ala Ile
            345                 350                 355 ctc gga acc gtc atc gca gaa aac ttc gca cct gag gtc cgc tac acc      1458
Leu Gly Thr Val Ile Ala Glu Asn Phe Ala Pro Glu Val Arg Tyr Thr
        360                 365                 370 ggc gct acc ctg ggt tac caa gtc gga gca gca ctc ttc ggc ggt acc      1506
Gly Ala Thr Leu Gly Tyr Gln Val Gly Ala Ala Leu Phe Gly Gly Thr
    375                 380                 385 gca ccc att atc gca gca tgg ctg ttc gaa atc tcc ggc gga caa tgg      1554
Ala Pro Ile Ile Ala Ala Trp Leu Phe Glu Ile Ser Gly Gly Gln Trp
390                 395                 400 tgg cca atc gcc gtc tac gtc gct gca tgt tgc ctt ctc tct gtg atc      1602
Trp Pro Ile Ala Val Tyr Val Ala Ala Cys Cys Leu Leu Ser Val Ile
405                 410                 415                 420 gcc tcg ttc ttc atc caa cgc gtc gcg cac caa gag aac taaaatctaa      1651
Ala Ser Phe Phe Ile Gln Arg Val Ala His Gln Glu Asn
            425                 430 gtaaaccccc tccgaaagga accacccatg gtgaaacgtc aactgcccaa ccccgcagaa    1711
ctactcgaac tcatgaagtt caaaaagcca gagctcaacg gcaagaaacg acgcctagac    1771
tccgcgctca ccatctacga cctgcgtaaa attgctaaac gacgcacccc agctgccgcg    1831
ttcgactaca ccgacggcgc agccgaggcc gaactctcaa tcacgcgcg acgtgaagca     1891 ttcgaaaaca tcgaattcca cccagacatc ctcaagcctg cagaacacgt agacaccacc    1951
acccaaatcc tgggcggaac ctcctccatg ccattcggca tcgcaccaac               2001

<210> SEQ ID NO 2
<211> LENGTH: 433
<212> TYPE: PRT
<213> ORGANISM: Corynebacterium glutamicum ATCC13032

<400> SEQUENCE: 2

Met Thr Thr Ala Val Asp Gln Asn Ser Pro Pro Lys Gln Gln Leu Asn
1               5                   10                  15

Lys Arg Val Leu Leu Gly Ser Leu Ser Gly Ser Val Ile Glu Trp Phe
            20                  25                  30

Asp Phe Leu Val Tyr Gly Thr Val Ala Ala Leu Val Phe Asn Lys Met
        35                  40                  45

Tyr Phe Pro Ser Gly Asn Glu Phe Leu Ser Thr Ile Leu Ala Tyr Ala
    50                  55                  60

Ser Phe Ser Leu Thr Phe Phe Arg Pro Ile Gly Gly Val Ile Phe
65                  70                  75                  80

Ala His Ile Gly Asp Arg Ile Gly Arg Lys Lys Thr Leu Phe Ile Thr
                85                  90                  95

Leu Met Leu Met Gly Gly Gly Thr Val Ala Ile Gly Leu Leu Pro Asp
            100                 105                 110

Tyr Asn Ala Ile Gly Ile Trp Ala Pro Ile Leu Leu Met Phe Leu Arg
        115                 120                 125

Ile Leu Gln Gly Ile Gly Ile Gly Gly Glu Trp Gly Gly Ala Leu Leu
    130                 135                 140

Leu Ala Tyr Glu Tyr Ala Pro Lys Lys Gln Arg Gly Leu Tyr Gly Ala
145                 150                 155                 160
```

-continued

```
Val Pro Gln Met Gly Ile Ser Leu Gly Met Leu Leu Ala Ala Gly Val
                165                 170                 175

Ile Ser Leu Leu Thr Leu Met Pro Glu Asp Gln Phe Leu Thr Trp Gly
            180                 185                 190

Trp Arg Ile Pro Phe Val Gly Ser Ile Leu Leu Val Phe Ile Gly Leu
        195                 200                 205

Phe Ile Arg Asn Gly Leu Asp Glu Thr Pro Glu Phe Lys Arg Ile Arg
    210                 215                 220

Asp Ser Gly Gln Gln Val Lys Met Pro Leu Lys Glu Val Leu Thr Lys
225                 230                 235                 240

Tyr Trp Pro Ala Val Leu Val Ser Ile Gly Ala Lys Ala Ala Glu Thr
                245                 250                 255

Gly Pro Phe Tyr Ile Phe Gly Thr Tyr Ile Val Ala Tyr Ala Thr Asn
            260                 265                 270

Phe Leu Asn Ile Arg Asp Asn Ile Val Leu Leu Ala Val Ala Cys Ala
        275                 280                 285

Ala Leu Val Ala Thr Ile Trp Met Pro Leu Phe Gly Ser Phe Ser Asp
    290                 295                 300

Arg Val Asn Arg Ala Val Leu Tyr Arg Ile Cys Ala Ser Ala Thr Ile
305                 310                 315                 320

Val Leu Ile Val Pro Tyr Tyr Leu Val Leu Asn Thr Gly Glu Ile Trp
                325                 330                 335

Ala Leu Phe Ile Thr Thr Val Ile Gly Phe Gly Ile Leu Trp Gly Ser
            340                 345                 350

Val Asn Ala Ile Leu Gly Thr Val Ile Ala Glu Asn Phe Ala Pro Glu
        355                 360                 365

Val Arg Tyr Thr Gly Ala Thr Leu Gly Tyr Gln Val Gly Ala Ala Leu
    370                 375                 380

Phe Gly Gly Thr Ala Pro Ile Ile Ala Ala Trp Leu Phe Glu Ile Ser
385                 390                 395                 400

Gly Gly Gln Trp Trp Pro Ile Ala Val Tyr Val Ala Ala Cys Cys Leu
                405                 410                 415

Leu Ser Val Ile Ala Ser Phe Phe Ile Gln Arg Val Ala His Gln Glu
            420                 425                 430

Asn

<210> SEQ ID NO 3
<211> LENGTH: 2001
<212> TYPE: DNA
<213> ORGANISM: Corynebacterium glutamicum
<220> FEATURE:
<221> NAME/KEY: misc_feature
<222> LOCATION: (221)..(221)
<223> OTHER INFORMATION: position 221
<220> FEATURE:
<221> NAME/KEY: CDS
<222> LOCATION: (343)..(1641)
<223> OTHER INFORMATION: coding sequence of a variant of NCgl2816
<220> FEATURE:
<221> NAME/KEY: misc_feature
<222> LOCATION: (1000)..(1002)
<223> OTHER INFORMATION: tgc codon for cysteine
<220> FEATURE:
<221> NAME/KEY: misc_feature
<222> LOCATION: (1001)..(1001)
<223> OTHER INFORMATION: nucleobase guanine
<220> FEATURE:
<221> NAME/KEY: misc_feature
<222> LOCATION: (1642)..(1644)
<223> OTHER INFORMATION: taa stop codon
```

<400> SEQUENCE: 3

```
gccaccaggg attgggccgt acgattcaac gctctcatgg ccattcacgg tcacctacat      60
attcctgccg aaacccgcgt tgatggggta agccacgtgg aggtttcttt gggttacccc     120
tttgaaaaac acccacctca catgaagcgt ccgtggccgt ttccggtcat gcagattaac     180
taactctgtt gcttaaatgg gggtaattgg attcgactgt tttccacacc ccattgacaa     240
ttaaaggtga cacgccttac attcttgtgg tctgaccatg aggttgggcc aatcggtttc     300
agcccgttta ctcccgccgt ccgtttcaga gaagaggtca cc atg aca acc gca       354
                                                Met Thr Thr Ala
                                                  1
```

| gta | gat | caa | aac | tca | ccg | ccc | aag | cag | caa | ctc | aac | aag | cgc | gtc | ctg | 402 |
|---|---|---|---|---|---|---|---|---|---|---|---|---|---|---|---|---|
| Val | Asp | Gln | Asn | Ser | Pro | Pro | Lys | Gln | Gln | Leu | Asn | Lys | Arg | Val | Leu | |
| 5 | | | | 10 | | | | | 15 | | | | | | 20 | |

| ctg | ggc | agc | ttg | agt | ggc | agc | gtt | atc | gaa | tgg | ttc | gac | ttc | ctg | gtt | 450 |
|---|---|---|---|---|---|---|---|---|---|---|---|---|---|---|---|---|
| Leu | Gly | Ser | Leu | Ser | Gly | Ser | Val | Ile | Glu | Trp | Phe | Asp | Phe | Leu | Val | |
| | | | | 25 | | | | | 30 | | | | | | 35 | |

| tac | gga | acc | gtc | gcc | gcg | ctg | gtc | ttc | aac | aag | atg | tac | ttc | ccc | agc | 498 |
|---|---|---|---|---|---|---|---|---|---|---|---|---|---|---|---|---|
| Tyr | Gly | Thr | Val | Ala | Ala | Leu | Val | Phe | Asn | Lys | Met | Tyr | Phe | Pro | Ser | |
| | | | 40 | | | | | 45 | | | | | 50 | | | |

| ggc | aac | gag | ttc | ctc | tcc | aca | atc | ctg | gcg | tac | gca | tcc | ttc | tcc | ctg | 546 |
|---|---|---|---|---|---|---|---|---|---|---|---|---|---|---|---|---|
| Gly | Asn | Glu | Phe | Leu | Ser | Thr | Ile | Leu | Ala | Tyr | Ala | Ser | Phe | Ser | Leu | |
| | | 55 | | | | | 60 | | | | | 65 | | | | |

| acc | ttc | ttc | ttc | cgc | ccc | att | ggt | ggc | gtc | atc | ttc | gcc | cac | atc | ggc | 594 |
|---|---|---|---|---|---|---|---|---|---|---|---|---|---|---|---|---|
| Thr | Phe | Phe | Phe | Arg | Pro | Ile | Gly | Gly | Val | Ile | Phe | Ala | His | Ile | Gly | |
| | 70 | | | | | 75 | | | | | 80 | | | | | |

| gac | cgc | att | ggg | cgt | aag | aag | acc | ctg | ttc | atc | acc | ttg | atg | ctc | atg | 642 |
|---|---|---|---|---|---|---|---|---|---|---|---|---|---|---|---|---|
| Asp | Arg | Ile | Gly | Arg | Lys | Lys | Thr | Leu | Phe | Ile | Thr | Leu | Met | Leu | Met | |
| 85 | | | | 90 | | | | | 95 | | | | | 100 | | |

| ggt | ggc | ggc | acc | gtc | gcc | att | ggt | ttg | ctg | ccc | gac | tac | aac | gcc | atc | 690 |
|---|---|---|---|---|---|---|---|---|---|---|---|---|---|---|---|---|
| Gly | Gly | Gly | Thr | Val | Ala | Ile | Gly | Leu | Leu | Pro | Asp | Tyr | Asn | Ala | Ile | |
| | | | 105 | | | | | 110 | | | | | 115 | | | |

| ggc | att | tgg | gca | cca | atc | ctt | ctg | atg | ttc | ctc | cgc | att | ttg | cag | ggc | 738 |
|---|---|---|---|---|---|---|---|---|---|---|---|---|---|---|---|---|
| Gly | Ile | Trp | Ala | Pro | Ile | Leu | Leu | Met | Phe | Leu | Arg | Ile | Leu | Gln | Gly | |
| | | 120 | | | | | 125 | | | | | 130 | | | | |

| atc | gga | att | ggc | ggc | gaa | tgg | ggt | ggc | gca | ctg | ctc | ctg | gca | tac | gaa | 786 |
|---|---|---|---|---|---|---|---|---|---|---|---|---|---|---|---|---|
| Ile | Gly | Ile | Gly | Gly | Glu | Trp | Gly | Gly | Ala | Leu | Leu | Leu | Ala | Tyr | Glu | |
| | 135 | | | | | 140 | | | | | 145 | | | | | |

| tac | gct | cca | aag | aag | cag | cgt | ggg | ctc | tac | ggc | gca | gtt | cct | caa | atg | 834 |
|---|---|---|---|---|---|---|---|---|---|---|---|---|---|---|---|---|
| Tyr | Ala | Pro | Lys | Lys | Gln | Arg | Gly | Leu | Tyr | Gly | Ala | Val | Pro | Gln | Met | |
| | 150 | | | | | 155 | | | | | 160 | | | | | |

| ggc | att | tcc | ctg | ggc | atg | ctg | ctt | gca | gct | ggc | gtg | atc | tct | ctg | ctc | 882 |
|---|---|---|---|---|---|---|---|---|---|---|---|---|---|---|---|---|
| Gly | Ile | Ser | Leu | Gly | Met | Leu | Leu | Ala | Ala | Gly | Val | Ile | Ser | Leu | Leu | |
| 165 | | | | 170 | | | | | 175 | | | | | 180 | | |

| acc | ctc | atg | ccg | gaa | gat | cag | ttc | ctc | acc | tgg | ggc | tgg | cgc | atc | cca | 930 |
|---|---|---|---|---|---|---|---|---|---|---|---|---|---|---|---|---|
| Thr | Leu | Met | Pro | Glu | Asp | Gln | Phe | Leu | Thr | Trp | Gly | Trp | Arg | Ile | Pro | |
| | | | 185 | | | | | 190 | | | | | 195 | | | |

| ttc | gtc | gga | tcc | atc | ctc | cta | gtg | ttc | atc | ggc | ctg | ttc | atc | cga | aac | 978 |
|---|---|---|---|---|---|---|---|---|---|---|---|---|---|---|---|---|
| Phe | Val | Gly | Ser | Ile | Leu | Leu | Val | Phe | Ile | Gly | Leu | Phe | Ile | Arg | Asn | |
| | | 200 | | | | | 205 | | | | | 210 | | | | |

| ggc | ctt | gat | gaa | acc | ccc | gag | tgc | aag | cgt | atc | cgc | gat | tcc | ggc | cag | 1026 |
|---|---|---|---|---|---|---|---|---|---|---|---|---|---|---|---|---|
| Gly | Leu | Asp | Glu | Thr | Pro | Glu | Cys | Lys | Arg | Ile | Arg | Asp | Ser | Gly | Gln | |
| | 215 | | | | | 220 | | | | | 225 | | | | | |

| cag | gta | aag | atg | cct | ctg | aag | gaa | gtt | ctg | acc | aag | tac | tgg | cca | gcc | 1074 |
|---|---|---|---|---|---|---|---|---|---|---|---|---|---|---|---|---|
| Gln | Val | Lys | Met | Pro | Leu | Lys | Glu | Val | Leu | Thr | Lys | Tyr | Trp | Pro | Ala | |
| | 230 | | | | | 235 | | | | | 240 | | | | | |

| gtt | ctg | gtc | tcc | atc | ggc | gca | aaa | gct | gcc | gag | acc | ggc | ccc | ttc | tac | 1122 |
|---|---|---|---|---|---|---|---|---|---|---|---|---|---|---|---|---|
| Val | Leu | Val | Ser | Ile | Gly | Ala | Lys | Ala | Ala | Glu | Thr | Gly | Pro | Phe | Tyr | |
| 245 | | | | 250 | | | | | 255 | | | | | 260 | | |

```
atc ttc ggc acc tac atc gtt gct tac gca acc aac ttc ctg aac atc     1170
Ile Phe Gly Thr Tyr Ile Val Ala Tyr Ala Thr Asn Phe Leu Asn Ile
            265                 270                 275 cgc gac aac att gtc ctt ctg gca gtt gct tgc gcc gcc ctc gtt gcc     1218
Arg Asp Asn Ile Val Leu Leu Ala Val Ala Cys Ala Ala Leu Val Ala
            280                 285                 290 acc atc tgg atg cca ctg ttc gga tcc ttc tcc gac cgc gtc aac cgt     1266
Thr Ile Trp Met Pro Leu Phe Gly Ser Phe Ser Asp Arg Val Asn Arg
            295                 300                 305 gca gtg ctc tac agg atc tgt gca tcc gca acc atc gtg ctg att gtc     1314
Ala Val Leu Tyr Arg Ile Cys Ala Ser Ala Thr Ile Val Leu Ile Val
            310                 315                 320 cct tac tac ttg gtc ctc aac acc ggc gaa att tgg gca ctg ttt atc     1362
Pro Tyr Tyr Leu Val Leu Asn Thr Gly Glu Ile Trp Ala Leu Phe Ile
325                 330                 335                 340 act acc gtg att ggc ttc ggc atc ctc tgg ggt agc gtc aac gca atc     1410
Thr Thr Val Ile Gly Phe Gly Ile Leu Trp Gly Ser Val Asn Ala Ile
            345                 350                 355 ctc gga acc gtc atc gca gaa aac ttc gca cct gag gtc cgc tac acc     1458
Leu Gly Thr Val Ile Ala Glu Asn Phe Ala Pro Glu Val Arg Tyr Thr
            360                 365                 370 ggc gct acc ctg ggt tac caa gtc gga gca gca ctc ttc ggc ggt acc     1506
Gly Ala Thr Leu Gly Tyr Gln Val Gly Ala Ala Leu Phe Gly Gly Thr
            375                 380                 385 gca ccc att atc gca gca tgg ctg ttc gaa atc tcc ggc gga caa tgg     1554
Ala Pro Ile Ile Ala Ala Trp Leu Phe Glu Ile Ser Gly Gly Gln Trp
            390                 395                 400 tgg cca atc gcc gtc tac gtc gct gca tgt tgc ctt ctc tct gtg atc     1602
Trp Pro Ile Ala Val Tyr Val Ala Ala Cys Cys Leu Leu Ser Val Ile
405                 410                 415                 420 gcc tcg ttc ttc atc caa cgc gtc gcg cac caa gag aac taaaatctaa      1651
Ala Ser Phe Phe Ile Gln Arg Val Ala His Gln Glu Asn
            425                 430 gtaaaacccc tccgaaagga accacccatg gtgaaacgtc aactgcccaa ccccgcagaa   1711
ctactcgaac tcatgaagtt caaaaagcca gagctcaacg gcaagaaacg acgcctagac   1771
tccgcgctca ccatctacga cctgcgtaaa attgctaaac gacgcacccc agctgccgcg   1831
ttcgactaca ccgacggcgc agccgaggcc gaactctcaa tcacgcgcgc acgtgaagca   1891
ttcgaaaaca tcgaattcca cccagacatc ctcaagcctg cagaacacgt agacaccacc   1951
acccaaatcc tgggcggaac ctcctccatg ccattcggca tcgcaccaac               2001

<210> SEQ ID NO 4
<211> LENGTH: 433
<212> TYPE: PRT
<213> ORGANISM: Corynebacterium glutamicum

<400> SEQUENCE: 4

Met Thr Thr Ala Val Asp Gln Asn Ser Pro Lys Gln Gln Leu Asn
1               5                   10                  15

Lys Arg Val Leu Leu Gly Ser Leu Ser Gly Ser Val Ile Glu Trp Phe
            20                  25                  30

Asp Phe Leu Val Tyr Gly Thr Val Ala Ala Leu Val Phe Asn Lys Met
            35                  40                  45

Tyr Phe Pro Ser Gly Asn Glu Phe Leu Ser Thr Ile Leu Ala Tyr Ala
        50                  55                  60

Ser Phe Ser Leu Thr Phe Phe Arg Pro Ile Gly Gly Val Ile Phe
65                  70                  75                  80
```

```
Ala His Ile Gly Asp Arg Ile Gly Arg Lys Lys Thr Leu Phe Ile Thr
                85                  90                  95
Leu Met Leu Met Gly Gly Gly Thr Val Ala Ile Gly Leu Leu Pro Asp
            100                 105                 110
Tyr Asn Ala Ile Gly Ile Trp Ala Pro Ile Leu Leu Met Phe Leu Arg
        115                 120                 125
Ile Leu Gln Gly Ile Gly Ile Gly Gly Glu Trp Gly Gly Ala Leu Leu
    130                 135                 140
Leu Ala Tyr Glu Tyr Ala Pro Lys Lys Gln Arg Gly Leu Tyr Gly Ala
145                 150                 155                 160
Val Pro Gln Met Gly Ile Ser Leu Gly Met Leu Leu Ala Ala Gly Val
                165                 170                 175
Ile Ser Leu Leu Thr Leu Met Pro Glu Asp Gln Phe Leu Thr Trp Gly
            180                 185                 190
Trp Arg Ile Pro Phe Val Gly Ser Ile Leu Leu Val Phe Ile Gly Leu
        195                 200                 205
Phe Ile Arg Asn Gly Leu Asp Glu Thr Pro Glu Cys Lys Arg Ile Arg
    210                 215                 220
Asp Ser Gly Gln Gln Val Lys Met Pro Leu Lys Glu Val Leu Thr Lys
225                 230                 235                 240
Tyr Trp Pro Ala Val Leu Val Ser Ile Gly Ala Lys Ala Ala Glu Thr
                245                 250                 255
Gly Pro Phe Tyr Ile Phe Gly Thr Tyr Ile Val Ala Tyr Ala Thr Asn
            260                 265                 270
Phe Leu Asn Ile Arg Asp Asn Ile Val Leu Leu Ala Val Ala Cys Ala
        275                 280                 285
Ala Leu Val Ala Thr Ile Trp Met Pro Leu Phe Gly Ser Phe Ser Asp
    290                 295                 300
Arg Val Asn Arg Ala Val Leu Tyr Arg Ile Cys Ala Ser Ala Thr Ile
305                 310                 315                 320
Val Leu Ile Val Pro Tyr Tyr Leu Val Leu Asn Thr Gly Glu Ile Trp
                325                 330                 335
Ala Leu Phe Ile Thr Thr Val Ile Gly Phe Gly Ile Leu Trp Gly Ser
            340                 345                 350
Val Asn Ala Ile Leu Gly Thr Val Ile Ala Glu Asn Phe Ala Pro Glu
        355                 360                 365
Val Arg Tyr Thr Gly Ala Thr Leu Gly Tyr Gln Val Gly Ala Ala Leu
    370                 375                 380
Phe Gly Gly Thr Ala Pro Ile Ile Ala Ala Trp Leu Phe Glu Ile Ser
385                 390                 395                 400
Gly Gly Gln Trp Trp Pro Ile Ala Val Tyr Val Ala Ala Cys Cys Leu
                405                 410                 415
Leu Ser Val Ile Ala Ser Phe Phe Ile Gln Arg Val Ala His Gln Glu
            420                 425                 430
Asn
```

```
<210> SEQ ID NO 5
<211> LENGTH: 1266
<212> TYPE: DNA
<213> ORGANISM: Corynebacterium glutamicum ATCC13032
<220> FEATURE:
<221> NAME/KEY: CDS
<222> LOCATION: (1)..(1263)
<220> FEATURE:
<221> NAME/KEY: misc_feature
```

<222> LOCATION: (1264)..(1266)
<223> OTHER INFORMATION: taa stop codon

<400> SEQUENCE: 5

```
gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc     384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc     432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg     480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt     528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag     576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc     624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat     672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg     720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ttt acc     768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att     816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat     864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa     912
Ala Glu Ile Asn Ile Asp Met Val Leu Gln Asn Val Ser Ser Val Glu
```

| | | | | | | | | | | | | | | | | |
|---|---|---|---|---|---|---|---|---|---|---|---|---|---|---|---|---|
| | | 290 | | | | 295 | | | | | 300 | | | | | |
| gac | ggc | acc | acc | gac | atc | acc | ttc | acc | tgc | cct | cgt | tcc | gac | ggc | cgc | 960 |
| Asp | Gly | Thr | Thr | Asp | Ile | Thr | Phe | Thr | Cys | Pro | Arg | Ser | Asp | Gly | Arg | |
| 305 | | | | 310 | | | | | 315 | | | | | 320 | | |
| cgc | gcg | atg | gag | atc | ttg | aag | aag | ctt | cag | gtt | cag | ggc | aac | tgg | acc | 1008 |
| Arg | Ala | Met | Glu | Ile | Leu | Lys | Lys | Leu | Gln | Val | Gln | Gly | Asn | Trp | Thr | |
| | | | 325 | | | | | 330 | | | | | 335 | | | |
| aat | gtg | ctt | tac | gac | gac | cag | gtc | ggc | aaa | gtc | tcc | ctc | gtg | ggt | gct | 1056 |
| Asn | Val | Leu | Tyr | Asp | Asp | Gln | Val | Gly | Lys | Val | Ser | Leu | Val | Gly | Ala | |
| | 340 | | | | | 345 | | | | | 350 | | | | | |
| ggc | atg | aag | tct | cac | cca | ggt | gtt | acc | gca | gag | ttc | atg | gaa | gct | ctg | 1104 |
| Gly | Met | Lys | Ser | His | Pro | Gly | Val | Thr | Ala | Glu | Phe | Met | Glu | Ala | Leu | |
| 355 | | | | | 360 | | | | | 365 | | | | | | |
| cgc | gat | gtc | aac | gtg | aac | atc | gaa | ttg | att | tcc | acc | tct | gag | att | cgt | 1152 |
| Arg | Asp | Val | Asn | Val | Asn | Ile | Glu | Leu | Ile | Ser | Thr | Ser | Glu | Ile | Arg | |
| | 370 | | | | | 375 | | | | | 380 | | | | | |
| att | tcc | gtg | ctg | atc | cgt | gaa | gat | gat | ctg | gat | gct | gct | gca | cgt | gca | 1200 |
| Ile | Ser | Val | Leu | Ile | Arg | Glu | Asp | Asp | Leu | Asp | Ala | Ala | Ala | Arg | Ala | |
| 385 | | | | 390 | | | | | 395 | | | | | 400 | | |
| ttg | cat | gag | cag | ttc | cag | ctg | ggc | ggc | gaa | gac | gaa | gcc | gtc | gtt | tat | 1248 |
| Leu | His | Glu | Gln | Phe | Gln | Leu | Gly | Gly | Glu | Asp | Glu | Ala | Val | Val | Tyr | |
| | | | | 405 | | | | | 410 | | | | | 415 | | |
| gca | ggc | acc | gga | cgc | taa | | | | | | | | | | | 1266 |
| Ala | Gly | Thr | Gly | Arg | | | | | | | | | | | | |
| | | | 420 | | | | | | | | | | | | | |

<210> SEQ ID NO 6
<211> LENGTH: 421
<212> TYPE: PRT
<213> ORGANISM: Corynebacterium glutamicum ATCC13032

<400> SEQUENCE: 6

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly

```
                195                 200                 205
Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 7
<211> LENGTH: 1619
<212> TYPE: DNA
<213> ORGANISM: artificial sequence
<220> FEATURE:
<223> OTHER INFORMATION: polynucleotide comprising a mutated nucleotide
      sequence
<220> FEATURE:
<221> NAME/KEY: misc_feature
<222> LOCATION: (4)..(9)
<223> OTHER INFORMATION: recognition site for restriction endonuclease
      XbaI
<220> FEATURE:
<221> NAME/KEY: CDS
<222> LOCATION: (152)..(1450)
<223> OTHER INFORMATION: coding sequence of NCgl2816
<220> FEATURE:
<221> NAME/KEY: misc_feature
<222> LOCATION: (809)..(811)
<223> OTHER INFORMATION: tgc codon for cysteine
<220> FEATURE:
<221> NAME/KEY: misc_feature
<222> LOCATION: (810)..(810)
<223> OTHER INFORMATION: nucleobase guanine
<220> FEATURE:
<221> NAME/KEY: misc_feature
<222> LOCATION: (1451)..(1453)
<223> OTHER INFORMATION: taa stop codon
<220> FEATURE:
<221> NAME/KEY: misc_feature
<222> LOCATION: (1611)..(1616)
<223> OTHER INFORMATION: recognition site for restriction endonuclease
      XbaI
```

<400> SEQUENCE: 7

```
gcgtctagag ggtaattgga ttcgactgtt ttccacaccc cattgacaat taaaggtgac     60
acgccttaca ttcttgtggt ctgaccatga ggttgggcca atcggtttca gcccgtttac    120
tcccgccgtc cgtttcagag aagaggtcac c atg aca acc gca gta gat caa       172
                                   Met Thr Thr Ala Val Asp Gln
                                    1               5 aac tca ccg ccc aag cag caa ctc aac aag cgc gtc ctg ctg ggc agc      220
Asn Ser Pro Pro Lys Gln Gln Leu Asn Lys Arg Val Leu Leu Gly Ser
            10              15                  20 ttg agt ggc agc gtt atc gaa tgg ttc gac ttc ctg gtt tac gga acc      268
Leu Ser Gly Ser Val Ile Glu Trp Phe Asp Phe Leu Val Tyr Gly Thr
25              30                  35 gtc gcc gcg ctg gtc ttc aac aag atg tac ttc ccc agc ggc aac gag      316
Val Ala Ala Leu Val Phe Asn Lys Met Tyr Phe Pro Ser Gly Asn Glu
40              45                  50                  55 ttc ctc tcc aca atc ctg gcg tac gca tcc ttc tcc ctg acc ttc ttc      364
Phe Leu Ser Thr Ile Leu Ala Tyr Ala Ser Phe Ser Leu Thr Phe Phe
                60                  65                  70 ttc cgc ccc att ggt ggc gtc atc ttc gcc cac atc ggc gac cgc att      412
Phe Arg Pro Ile Gly Gly Val Ile Phe Ala His Ile Gly Asp Arg Ile
        75                  80                  85 ggg cgt aag aag acc ctg ttc atc acc ttg atg ctc atg ggt ggc ggc      460
Gly Arg Lys Lys Thr Leu Phe Ile Thr Leu Met Leu Met Gly Gly Gly
            90                  95                  100 acc gtc gcc att ggt ttg ctg ccc gac tac aac gcc atc ggc att tgg      508
Thr Val Ala Ile Gly Leu Leu Pro Asp Tyr Asn Ala Ile Gly Ile Trp
105                 110                 115 gca cca atc ctt ctg atg ttc ctc cgc att ttg cag ggc atc gga att      556
Ala Pro Ile Leu Leu Met Phe Leu Arg Ile Leu Gln Gly Ile Gly Ile
120                 125                 130                 135 ggc ggc gaa tgg ggt ggc gca ctc ctg gca tac gaa tac gct cca          604
Gly Gly Glu Trp Gly Gly Ala Leu Leu Ala Tyr Glu Tyr Ala Pro
                140                 145                 150 aag aag cag cgt ggg ctc tac ggc gca gtt cct caa atg ggc att tcc      652
Lys Lys Gln Arg Gly Leu Tyr Gly Ala Val Pro Gln Met Gly Ile Ser
            155                 160                 165 ctg ggc atg ctg ctt gca gct ggc gtg atc tct ctg ctc acc ctc atg      700
Leu Gly Met Leu Leu Ala Ala Gly Val Ile Ser Leu Leu Thr Leu Met
        170                 175                 180 ccg gaa gat cag ttc ctc acc tgg ggc tgg cgc atc cca ttc gtc gga      748
Pro Glu Asp Gln Phe Leu Thr Trp Gly Trp Arg Ile Pro Phe Val Gly
185                 190                 195 tcc atc ctc cta gtg ttc atc ggc ctg ttc atc cga aac ggc ctt gat      796
Ser Ile Leu Leu Val Phe Ile Gly Leu Phe Ile Arg Asn Gly Leu Asp
200                 205                 210                 215 gaa acc ccc gag tgc aag cgt atc cgc gat tcc ggc cag cag gta aag      844
Glu Thr Pro Glu Cys Lys Arg Ile Arg Asp Ser Gly Gln Gln Val Lys
                220                 225                 230 atg cct ctg aag gaa gtt ctg acc aag tac tgg cca gcc gtt ctg gtc      892
Met Pro Leu Lys Glu Val Leu Thr Lys Tyr Trp Pro Ala Val Leu Val
            235                 240                 245 tcc atc ggc gca aaa gct gcc gag acc ggc ccc ttc tac atc ttc ggc      940
Ser Ile Gly Ala Lys Ala Ala Glu Thr Gly Pro Phe Tyr Ile Phe Gly
        250                 255                 260 acc tac atc gtt gct tac gca acc aac ttc ctg aac atc cgc gac aac      988
Thr Tyr Ile Val Ala Tyr Ala Thr Asn Phe Leu Asn Ile Arg Asp Asn
265                 270                 275 att gtc ctt ctg gca gtt gct tgc gcc gcc ctc gtt gcc acc atc tgg     1036
Ile Val Leu Leu Ala Val Ala Cys Ala Ala Leu Val Ala Thr Ile Trp
```

```
atg cca ctg ttc gga tcc ttc tcc gac cgc gtc aac cgt gca gtg ctc    1084
Met Pro Leu Phe Gly Ser Phe Ser Asp Arg Val Asn Arg Ala Val Leu
            300                 305                 310 tac agg atc tgt gca tcc gca acc atc gtg ctg att gtc cct tac tac    1132
Tyr Arg Ile Cys Ala Ser Ala Thr Ile Val Leu Ile Val Pro Tyr Tyr
        315                 320                 325 ttg gtc ctc aac acc ggc gaa att tgg gca ctg ttt atc act acc gtg    1180
Leu Val Leu Asn Thr Gly Glu Ile Trp Ala Leu Phe Ile Thr Thr Val
            330                 335                 340 att ggc ttc ggc atc ctc tgg ggt agc gtc aac gca atc ctc gga acc    1228
Ile Gly Phe Gly Ile Leu Trp Gly Ser Val Asn Ala Ile Leu Gly Thr
        345                 350                 355 gtc atc gca gaa aac ttc gca cct gag gtc cgc tac acc ggc gct acc    1276
Val Ile Ala Glu Asn Phe Ala Pro Glu Val Arg Tyr Thr Gly Ala Thr
360                 365                 370                 375 ctg ggt tac caa gtc gga gca gca ctc ttc ggc ggt acc gca ccc att    1324
Leu Gly Tyr Gln Val Gly Ala Ala Leu Phe Gly Gly Thr Ala Pro Ile
            380                 385                 390 atc gca gca tgg ctg ttc gaa atc tcc ggc gga caa tgg tgg cca atc    1372
Ile Ala Ala Trp Leu Phe Glu Ile Ser Gly Gly Gln Trp Trp Pro Ile
        395                 400                 405 gcc gtc tac gtc gct gca tgt tgc ctt ctc tct gtg atc gcc tcg ttc    1420
Ala Val Tyr Val Ala Ala Cys Cys Leu Leu Ser Val Ile Ala Ser Phe
            410                 415                 420 ttc atc caa cgc gtc gcg cac caa gag aac taaaatctaa gtaaaacccc      1470
Phe Ile Gln Arg Val Ala His Gln Glu Asn
        425                 430 tccgaaagga accacccatg gtgaaacgtc aactgcccaa ccccgcagaa ctactcgaac  1530
tcatgaagtt caaaaagcca gagctcaacg gcaagaaacg acgcctagac tccgcgctca  1590
ccatctacga cctgcgtaaa tctagagcc                                    1619
```

<210> SEQ ID NO 8
<211> LENGTH: 433
<212> TYPE: PRT
<213> ORGANISM: artificial sequence
<220> FEATURE:
<223> OTHER INFORMATION: Synthetic Construct

<400> SEQUENCE: 8

Met Thr Thr Ala Val Asp Gln Asn Ser Pro Pro Lys Gln Gln Leu Asn
1               5                   10                  15

Lys Arg Val Leu Leu Gly Ser Leu Ser Gly Ser Val Ile Glu Trp Phe
            20                  25                  30

Asp Phe Leu Val Tyr Gly Thr Val Ala Ala Leu Val Phe Asn Lys Met
        35                  40                  45

Tyr Phe Pro Ser Gly Asn Glu Phe Leu Ser Thr Ile Leu Ala Tyr Ala
    50                  55                  60

Ser Phe Ser Leu Thr Phe Phe Arg Pro Ile Gly Gly Val Ile Phe
65                  70                  75                  80

Ala His Ile Gly Asp Arg Ile Gly Arg Lys Lys Thr Leu Phe Ile Thr
                85                  90                  95

Leu Met Leu Met Gly Gly Thr Val Ala Ile Gly Leu Leu Pro Asp
            100                 105                 110

Tyr Asn Ala Ile Gly Ile Trp Ala Pro Ile Leu Leu Met Phe Leu Arg
        115                 120                 125

Ile Leu Gln Gly Ile Gly Ile Gly Gly Glu Trp Gly Gly Ala Leu Leu

```
            130             135             140
Leu Ala Tyr Glu Tyr Ala Pro Lys Lys Gln Arg Gly Leu Tyr Gly Ala
145                     150                 155                 160

Val Pro Gln Met Gly Ile Ser Leu Gly Met Leu Leu Ala Ala Gly Val
                165                 170                 175

Ile Ser Leu Leu Thr Leu Met Pro Glu Asp Gln Phe Leu Thr Trp Gly
                180                 185                 190

Trp Arg Ile Pro Phe Val Gly Ser Ile Leu Leu Val Phe Ile Gly Leu
                195                 200                 205

Phe Ile Arg Asn Gly Leu Asp Glu Thr Pro Glu Cys Lys Arg Ile Arg
210                     215                 220

Asp Ser Gly Gln Gln Val Lys Met Pro Leu Lys Glu Val Leu Thr Lys
225                     230                 235                 240

Tyr Trp Pro Ala Val Leu Val Ser Ile Gly Ala Lys Ala Ala Glu Thr
                245                 250                 255

Gly Pro Phe Tyr Ile Phe Gly Thr Tyr Ile Val Ala Tyr Ala Thr Asn
                260                 265                 270

Phe Leu Asn Ile Arg Asp Asn Ile Val Leu Leu Ala Val Ala Cys Ala
                275                 280                 285

Ala Leu Val Ala Thr Ile Trp Met Pro Leu Phe Gly Ser Phe Ser Asp
290                     295                 300

Arg Val Asn Arg Ala Val Leu Tyr Arg Ile Cys Ala Ser Ala Thr Ile
305                     310                 315                 320

Val Leu Ile Val Pro Tyr Tyr Leu Val Leu Asn Thr Gly Glu Ile Trp
                325                 330                 335

Ala Leu Phe Ile Thr Thr Val Ile Gly Phe Gly Ile Leu Trp Gly Ser
                340                 345                 350

Val Asn Ala Ile Leu Gly Thr Val Ile Ala Glu Asn Phe Ala Pro Glu
                355                 360                 365

Val Arg Tyr Thr Gly Ala Thr Leu Gly Tyr Gln Val Gly Ala Ala Leu
                370                 375                 380

Phe Gly Gly Thr Ala Pro Ile Ile Ala Ala Trp Leu Phe Glu Ile Ser
385                     390                 395                 400

Gly Gly Gln Trp Trp Pro Ile Ala Val Tyr Val Ala Ala Cys Cys Leu
                405                 410                 415

Leu Ser Val Ile Ala Ser Phe Phe Ile Gln Arg Val Ala His Gln Glu
                420                 425                 430

Asn
```

METHOD FOR THE FERMENTATIVE PRODUCTION OF L-LYSINE BY MODIFIED *CORYNEBACTERIUM GLUTAMICUM*

CROSS-REFERENCE TO RELATED APPLICATIONS

The present application claims the benefit of the European Application EP18196725.8, filed on Sep. 26, 2018, which is incorporated by reference in its entirety.

REFERENCE TO A SEQUENCE LISTING

The present application is accompanied by an ASCII text file as a computer readable form containing the sequence listing, titled "2019-08-26-SEQ-as-filed," created on Aug. 15, 2019, 8:27:35 AM, with the file size of 44,748 bytes, which is incorporated by reference in its entirety. Applicants hereby state that the information recorded in computer readable form is identical to the written (on paper or compact disc) sequence listing.

BACKGROUND OF THE INVENTION

Field of the Invention

L-lysine is used in human medicine, in the pharmaceutical industry, in the food industry and particularly in nutrition of animals.

Discussion of the Background

L-lysine is produced by fermentation of strains of the species *Corynebacterium glutamicurn* (*C. glutamicum*). Because of the great economic importance, work is continually being done on improving the production methods. Improvements may relate to the fermentation technology such as e.g. stirring and supplying oxygen, or to the composition of the nutrient media e.g. the sugar concentration during fermentation, or to the processing of the fermentation broth to a suitable product form by e.g. drying and, granulating the fermentation broth or ion exchange chromatography or may relate to the intrinsic performance properties of the microorganism itself.

The methods used for improving the performance properties of these microorganisms are those of mutagenesis, selection and screening of mutants. The strains obtained in this way are resistant to anti-metabolites or are auxotrophic for metabolites of regulatory importance and produce L-lysine.

Methods of recombinant DNA technology have likewise been used for a number of years for improvement of L-lysine-producing strains of the species *Corynebacterium glutamicum*, by modifying, i.e. enhancing or attenuating, individual genes involved in L-lysine biosynthesis and investigating the effect on L-lysine production (Sanchez et al. The Journal of antibiotics (2018) 71, 26-36; published online 1 Nov. 2017).

The nucleotide sequences of the chromosomes of various bacteria or strains respective of the species *Corynebacterium glutamicum*, and their analysis have been disclosed. This information is available at publicly accessible databases and may be used for strain development purposes. One such database is the GenBank data base of the NCBI (National Center for Biotechnology information, U.S. National Library of Medicine 8600 Rockville Pike, Bethesda Md., 20894 USA).

During the annotation procedure for a sequenced chromosome of an organism identified structures such as e.g. genes or coding sequences are furnished with a unique identifier called locus_tag by the supplier of the information to the data base.

The nucleotide sequence of the *Corynebacterium glutarmicum*, ATCC13032 chromosome and its analysis were described by Ikeda and Nakagawa (Applied Microbiology and Biotechnology 62, 99-109 (2003)) and in EP1108790. The information is available at the NCBI under accession number NC_003450. In the chromosome sequence disclosed under accession number NC_003450 locus_tag NCgl2816 identifies a nucleotide sequence coding for an integral membrane transport protein. It is further annotated that the protein is similar to permeases of the major facilitator superfamily. The amino acid sequence of the polypeptide is available wider the identifier NP_602106.1, where it is described as an integral membrane transport protein and provisionally as a putative sialic acid transporter. In EP1108790 A2 the coding sequence is disclosed under sequence 3216. The amino acid sequence is disclosed under SEQ ID NO: 6716. Further EP1108790 A2 states that the homologous gene in *Escherichia coli* is the shiA gene encoding a shikimate transport protein (see table 1 of EP1108790 A2).

The nucleotide sequences of locus tag NCgl2816 and sequence 3216 of EP1108790 are identical.

The nucleotide sequence of the *Corynebacterium glutamicum* ATCC13032 chromosome and its analysis were independently described by Kalinowski et al. (Journal of Biotechnology 104 (1-3), 5-25 (2003)). The information is available at the NCBI under accession number NC_006958. Locus_tag CGTRNA_RS14420 identifies a nucleotide sequence coding for a gene product described as MFS transporter. The old_locus_tag designation cg3226 is also used in the art. The amino acid sequence of the polypeptide is available under the identifier WP_011015489, where it is provisionally described as a putative sialic acid transporter.

The nucleotide sequences of Locus_tag NCgl2816 and CGTRNA_RS14420 are identical.

The term "MFS" is the abbreviation for "Major Facilitator Superfamily." According to the conserved domain database at the NCBI (see database entry cd06174) the term denotes a large and diverse group of secondary transporters that includes uniporters, symporters, and antiporters, which facilitate the transport across cytoplasmic or internal membranes of a variety of substrates including ions, sugar phosphates, drugs, neurotransmitters, nucleosides, amino acids, and peptides. Pao et al. (Microbiology and Molecular Biology Reviews 62(1), 1-34 (1998)) present a summary of this group of proteins.

Information concerning transcription signals in *Corynebacterium glutamicum*, e.g.—10 region of a promoter, or transcriptional start site (TSS) of the gene identified by old_locus_tag cg3226 can be found in Pfeifer-Sancar et al. (BMC Genomics 14:888 (2013)), Albersmeier et al. (Journal of Biotechnology 257 (2017) 99-109) or Mentz et al. (BMC Genomics 2013, 14:714). According to these teachings said transcription signals are contained in the sequence from position 221 to 342 of SEQ ID NO:1 of the sequence listing.

Stamen et al. (Applied and Environmental Microbiology 71(10), 5920-5928 (2005)) provide experimental indications that NCgl2816 putatively codes for a lactate permease or a putative transport protein for the uptake of L-lactate from the medium into the cell respectively. NCgl2816 together with the lldD-gene, which encodes a quinone-dependent L-lactate dehydrogenase, forms the NCgl2816-lldD operon.

Further information concerning this operon and the regulation of its expression can be found by Georgi et al. (Journal of Bacteriology 190(3), 963-971 (2008)).

SUMMARY OF THE INVENTION

Object of the present invention is to provide new measures for the fermentative production of L-lysine by bacteria of the species Corynebacterium glutamicum.

To achieve the object outlined above the present invention makes available a novel method for the fermentative production of L-lysine using bacteria of the species Corynebacterium glutamicum, having the ability to excrete L-lysine, containing in their chromosome a polynucleotide encoding a polypeptide comprising the amino acid sequence of SEQ ID NO:2 wherein the amino acid at position 220 of the amino acid sequence of the polypeptide is any proteinogenic amino acid different from phenylalanine.

Accordingly, the present invention provides a method for the fermentative production of L-lysine comprising the steps of a) providing a bacterium of the species Corynebacterium glutamicum, having the ability to excrete L-lysine, containing in its chromosome a polynucleotide encoding a polypeptide comprising the amino acid sequence of SEQ ID NO:2, wherein the amino acid phenylalanine at position 220 is substituted by a different proteinogenic amino acid, preferably by cysteine, b) cultivating the bacterium in a suitable medium under suitable conditions, and c) accumulating the L-lysine in the medium to form an L-lysine containing fermentation broth.

The amino acid sequence of SEQ ID NO:2, wherein the amino acid phenylalanine at position 220 is substituted by cysteine, is shown in SEQ ID NO:4.

The present invention includes the following embodiments:

1. A method for the fermentative production of L-lysine comprising the steps of a) providing a bacterium of the species Corynebacterium glutamicum having the ability to excrete L-lysine containing in its chromosome a polynucleotide encoding a polypeptide comprising the amino acid sequence of SEQ ID NO:2, wherein the amino acid phenylalanine at position 220 is substituted by a different proteinogenic amino acid, b) cultivating the bacterium in a suitable medium under suitable conditions, and c) accumulating said L-lysine in the medium to form an L-lysine containing fermentation broth.

2. The method of embodiment 1, wherein in the bacterium the amino acid at position 220 of the amino acid sequence of SEQ ID NO:2 is cysteine.

3. The method of embodiment 2, wherein in the bacterium the polynucleotide encoding said amino acid sequence comprises the nucleotide sequence of positions 343 to 1641 of SEQ ID NO:1 with the nucleobases at positions 1000 to 1002 being tgt or tgc.

4. The method of embodiment 3, wherein the nucleobases at positions 1000 to 1002 are tgc.

5. The method of embodiment 2, wherein in the bacterium the polynucleotide encoding said amino acid sequence comprises the nucleotide sequence of positions 343 to 1644 of SEQ ID NO:1 with the nucleobases at positions 1000 to 1002 being tgt or tgc.

6. The method of embodiment 5, wherein the nucleobases at positions 1002 to 1004 are tgc.

7. The method of embodiment 2, wherein in the bacterium the polynucleotide encoding said amino acid sequence comprises the nucleotide sequence of positions 221 to 1644 of SEQ ID NO:1 with the nucleobases at positions 1000 to 1002 being tgt or tgc.

8. The method of embodiment 7, wherein the nucleobases at positions 1000 to 1002 are tgc.

9. The method as recited in any of the preceding embodiments, further comprising the manufacturing of an L-lysine containing product from the fermentation broth.

10. The method as recited in any of the preceding embodiments, further comprising extracting or substantially eliminating water from the fermentation broth.

11. The method of embodiment 10, wherein said manufacturing comprises a purification step.

DETAILED DESCRIPTION OF THE INVENTION

It was found that the modified bacteria, provided in the method according to the invention, excreted L-lysine into a suitable medium under suitable fermentation conditions in an increased yield as compared to the unmodified bacterium.

It is clear that a higher product concentration facilitates product manufacturing e.g. purification and isolation. An increased product yield reduces the amount of raw material required. An increased product formation rate reduces the time required for a fermentation run thus increasing the availability of a given fermenter.

The method according to the invention thus contributes to the improvement of technical and economic aspects of the manufacturing of L-lysine or L-lysine containing products.

In a preferred embodiment the bacterium provided in the method according to the invention contains in its chromosome a polynucleotide encoding an amino acid sequence of a polypeptide comprising the nucleotide sequence of positions 343 to 1641 of SEQ ID NO:1 with the nucleobases from position 1000 to 1002 being tgt or tgc, preferably tgc.

Particularly preferred is the nucleotide sequence of positions 343 to 1641 of SEQ ID NO:1 with the nucleobase at position 1001 being guanine (g).

The nucleotide sequence of positions 343 to 1641 of SEQ ID NO:1 with the nucleobases from positions 1000 to 1002, being tgc is identical to the nucleotide sequence of positions 343 to 1641 of SEQ ID NO:3.

In another preferred embodiment the bacterium provided in the method according to the invention contains in its chromosome a polynucleotide encoding an amino acid sequence of a polypeptide comprising the nucleotide sequence of positions 343 to 1644 of SEQ ID NO:1 with the nucleobases from positions 1000 to 1002 being tgt or tgc, preferably tgc.

Particularly preferred is the nucleotide sequence of positions 343 to 1644 of SEQ ID NO:1 with the nucleobase at position 1001 being guanine (g).

The nucleotide sequence of positions 343 to 1644 of SEQ ID NO:1 with the nucleobases from positions 1000 to 1002 being tgc is identical to the nucleotide sequence of positions 343 to 1644 of SEQ ID NO:3.

In another preferred embodiment the bacterium provided in the method according to the invention contains in its chromosome a polynucleotide encoding an amino acid sequence of a polypeptide comprising the nucleotide sequence of positions 221 to 1644 of SEQ ID NO:1 with the nucleobases from positions 1000 to 1002 being tgt or tgc, preferably tgc.

Particularly preferred is the nucleotide sequence of positions 221 to 1641 of SEQ ID NO:1 with the nucleobase at position 1001 being guanine (g).

The nucleotide sequence of positions 221 to 1644 of SEQ ID NO:1 with the nucleobases from positions 1000 to 1002 being tgc is identical to the nucleotide sequence of positions 221 to 1644 of SEQ ID NO:3.

The term L-lysine, where mentioned herein, in particular in the context of product formation, also comprises their ionic forms and salts, for example L-lysine mono hydrochloride or L-lysine sulfate.

Suitable bacteria for the method of this invention are L-lysine excreting strains of *Corynebacterium glutamicum*, for example L-lysine excreting strains obtained by one or several steps of strain development from strain ATCC13032 and the like and modified as described in this invention.

Strain ATCC13032 (also available as DSM20300) is the taxonomic type strain of the species *Corynebacterium glutamicum*.

L-lysine excreting strains of the species *Corynebacterium glutamicum* are widely known in the art and can be modified as described in the present invention. For example, U.S. Pat. No. 7,338,790 B2 describes strain DM1797. It is deposited according to the Budapest treaty at the DSMZ under accession number DSM16833. DM1797 is an aminoethylcystein resistant mutant of strain ATCC13032 obtained after N'-methyl-N-nitro-nitrosoguanidine mutagenesis. For example, Blombach et al. (Applied and Environmental Microbiology 75(2), 419-427, 2009) describe strain DM1933 (deposited under accession number DSM25442 according to the Budapest treaty). Strain DM1933 was obtained from ATCC13032 by several steps of strain development. Furthermore L-lysine excreting *Corynebacterium glutamicum* strain DM2031, deposited according to the Budapest Treaty as DSM32514 may be used. Strain DM2031 is a further developed derivative of DM1933 having enhanced L-lysine excretion ability. Other L-lysine excreting *Corynebacterium glutamicum* strains are e.g. described in WO2008033001 and EP0841395.

L-lysine excreting strains of the species *Corynebacterium glutamicum* typically contain a polynucleotide coding for a feedback resistant aspartokinase polypeptide variant. A feedback resistant aspartokinase polypeptide variant means an aspartokinase which is less sensitive, or desensitized respectively, to inhibition by mixtures of L-lysine and L-threonine, e.g. 10 mM each, or mixtures of the L-lysine analogue S-(2-aminoethyl)-L-cysteine and L-threonine, e.g. 50 mM S-(2-aminoethyl)-L-cysteine and 10 mM threonine, when compared to the wild form of the enzyme, which is contained in wild strains like for example ATCC13032, ATCC14067 and ATCC13869. The EC number for aspartokinase is EC 2.7.2.4. Descriptions of polynucleotides of *Corynebacterium glutamicum* encoding a feedback resistant aspartokinase polypeptide variant are for example given in U.S. Pat. Nos. 5,688,671, 6,844,176 and 6,893,848. A summarizing list can be found inter alia in WO2009141330. The symbol used in the art for a gene coding for an aspartokinase polypeptide is lysC. In case the gene codes for a feedback resistant polypeptide variant the art typically uses symbols like lysC$^{fbr}$ with fbr indicating feedback resistance.

Accordingly, said L-lysine excreting strains of the species *Corynebacterium glutamicum* modified as described in the present invention preferably contain at least one copy of a polynucleotide coding for a feedback resistant aspartokinase polypeptide.

SEQ ID NO:5 shows the nucleotide sequence of the coding sequence of the aspartokinase polypeptide of strain ATCC13032 and SEQ ID NO:6 the amino acid sequence of the encoded polypeptide. It is known in the art (see U.S. Pat. No. 6,893,848) that exchange of the amino acid Thr at position 311 of SEQ NO:6 for Ile imparts the enzyme feedback resistance to inhibition by mixtures of L-lysine and L-threonine.

Accordingly, it is preferred that the amino acid sequence of said feedback resistant aspartokinase polypeptide comprises the amino acid sequence of SEQ ID NO:6 containing isoleucine at position 311.

This amino acid exchange can be achieved by exchanging the nucleobase cytosine (c) at position 932 of SEQ ID NO:5 to give thymine (t). The acc codon for threonine is thus altered to the atc codon for isoleucine.

It is further known in the art that exchange of the gtg start codon of the coding sequence for the aspartokinase polypeptide for atg enhances expression of the polypeptide (see e.g. EP2796555).

Accordingly, it is preferred that the sequence coding for a feedback resistant aspartokinase polypeptide begins with an atg start codon.

The term DSM denotes the depository Deutsche Sammlung für Mikroorganismen und Zellkulturen located in Braunschweig, Germany. The term ATCC denotes the depository American Type Culture Collection located in Manassas, Va., US.

For sequence analysis of polynucleotides and polypeptides, e.g. sequence alignments the Clustal W program (Larkin et al.: Clustal W and Clustal X version 2.0. In: Bioinformatics 23, 2947-2948 (2007)) or public software such as the CLC Genomics Workbench (Qiagen, Hilden, Germany) or the program MUSCLE provided by the European Bioinformatics Institute (EMBL-EBI, Hinxton, UK) may be used.

*Corynebacterium glutamicum*, in particular strain ATCC13032 and L-lysine excreting strains obtained therefrom during a strain development program, contain in their chromosome a, in particular one, gene encoding a polypeptide comprising the amino acid sequence of SEQ ID NO:2. The function of the polypeptide is broadly described as an MFS transporter in the art. The coding sequence is shown in SEQ ID NO:1, positions 343 to 1641. The coding sequence may contain silent mutations which do not alter the amino acid sequence of the polypeptide. This context is also known as degeneracy of the genetic code in the art.

During the work for the present invention it was found that modifying L-lysine excreting bacteria of the species *Corynebacterium glutamicum* by exchanging the amino acid phenylalanine at position 220 of the encoded amino acid sequence of the polypeptide shown in SEQ ID NO:2 for a different proteinogenic amino acid, preferably cysteine, increased their ability to excrete L-lysine in a fermentative process as compared to the unmodified bacterium.

The skilled artisan is aware of a number of methods of mutagenesis how to achieve said modification in the *Corynebacterium glutamicum*.

A mutant bacterium can be obtained by classical in vivo mutagenesis executed with cell populations of strains of *Corynebacterium glutamicum* using mutagenic substances, e.g. N-methyl-N'-nitro-N-nitrosoguanidine, or ultraviolet light.

The nucleotide sequence comprising the site of mutagenesis within the gene can be amplified by PCR using primers selected from SEQ ID NO:1 or SEQ ID NO:3. By sequencing the PCR product the desired mutants are identified. Details concerning this approach can be found inter glia in U.S. Pat. No. 7,754,446. Real-time PCR in combination with FRET hybridization probes may also be used for mutation detection. The term FRET is the abbreviation for fluorescence resonance energy transfer. Cyril D S Mamotte (The Clinical Biochemist Reviews 27, 63-75 (2006)) reviews the identification of single nucleotide substitutions using this method. Further summaries concerning this method may be found in the textbook Lewin's Genes XII by Jocelyn E. Krebs, Elliott S. Goldstein and Stephan T. Kilpatrick (Jones and Bartlett Publishers, US, 2018) or elsewhere in the art.

Another common method of mutating genes of *Corynebacterium glutamicum* is the method of gene replacement described by Schafer et al. (Gene 145, 69-73 (1994)).

Peters-Wendisch et al. (Microbiology 144, 915-927 (1998)) used the gene replacement method to inactivate the pyc gene of *Corynebacterium glutamicum* encoding pyruvate carboxylase. In U.S. Pat. No. 7,585,650 the method was applied to the zwf gene to realize an amino acid exchange at position 321 of the amino acid sequence of the Zwf sub-unit of the glucose 6-phosphate dehydrogenase. In U.S. Pat. No. 7,754,446 the method was applied to the rel gene to realize an amino acid exchange at position 38 of the amino acid sequence of the GTP-pyrophosphate kinase polypeptide.

In the gene replacement method, a mutation, for example, a deletion, insertion or substitution of at least one nucleobase, is provided by an isolated polynucleotide comprising the nucleotide sequence of the gene in question or a part thereof containing the mutation.

In the context of the present invention the nucleotide sequence of the gene in question is the gene identified by NCgl2816.

In the context of the present invention the mutation is a substitution of at least one nucleobase located in the codon specifying the amino acid phenylalanine at position 220 of the encoded amino acid sequence (see SEQ ID NO:1 and SEQ ID NO:2) of the polypeptide.

As a consequence of said mutation the codon specifies a proteinogenic amino acid different from phenylalanine, preferably cysteine. The codons specifying cysteine are tgt or tgc. The codon tgc is preferred.

The codon for the amino acid at position 220 has the position from 1000 to 1002 in SEQ ID NO:1 or SEQ ID NO:3. The nucleotide sequence from position 1000 to 1002, in particular the nucleotide at position 1001, may also be referred to as site of mutation.

The mutated nucleotide sequence of the gene in question or a part thereof containing the mutation comprises i) a nucleotide sequence at the 5'-end of the site of mutation, which is also referred to as 5'-flanking sequence or upstream sequence in the art, ii) a nucleotide sequence at the 3'-end of the site of mutation, which is also referred to as 3'-flanking sequence or downstream sequence in the art, and iii) the nucleotide sequence of the site of mutation between and ii).

These 5'-flanking sequence and 3'-flanking sequence required for homologous recombination typically have a length of at least 200 bp, at least 400 bp, at least 600 bp or at least 800 bp. The maximum length typically is 1000 bp, 1500 bp or 2000 bp.

An example of a polynucleotide comprising a mutated nucleotide sequence in the context of the present invention is shown in SEQ ID NO:7. The nucleotide sequence of SEQ ID NO:7 from positions 10 to 1610 corresponds to SEQ ID NO:3 from positions 201 to 1801. The polynucleotide shown in SEQ ID NO:7 contains at its 5'- and 3'-end recognition sites for restriction endonucleases useful for cloning purposes. SEQ ID NO:7 contains the coding sequence of a variant of the NCgl2816 polypeptide described in this invention. The 5'-flanking sequence consists of the nucleotide sequence from positions 10 to 809 of SEQ ID NO:7. The 3'-flanking sequence consists of the nucleotide sequence from positions 811 to 1610 of SEQ ID NO:7. The site of mutation is at position 810 of SEQ ID NO:7.

The mutated nucleotide sequence provided is cloned into a plasmid vector, e.g. pK18mobsacT3 described by Schafer et al. (Gene 145, 69-73 (1994)), which is not capable of autonomous replication in *Corynebacterium glutamicum*. This plasmid vector comprising the mutated nucleotide sequence is subsequently transferred into the desired strain of *Corynebacterium glutamicum* by transformation using electroporation or conjugation. After two events of homologous recombination comprising a recombination event within the 5'-flanking sequence provided by the plasmid vector with the homologous sequence of the *Corynebacterium glutamicum* chromosome and a recombination event within the 3'-flanking sequence provided by the plasmid vector with the homologous sequence of the *Corynebacterium glutamicum* chromosome, one effecting integration and one effecting excision of the plasmid vector, the mutation is incorporated in the *Corynebacterium glutamicum* chromosome. Thus, the nucleotide sequence of the gene in question contained in the chromosome of said desired strain is replaced by the mutated nucleotide sequence.

An event of homologous recombination may also be referred to as crossing over.

It is preferred that the L-lysine excreting *Corynebacterium glutamicum* strains provided for the method of the present invention have the ability to excrete ≥0.25 g/l, preferably ≥0.5 g/l, particularly preferred ≥1.0 g/l, very particularly preferred 2.0 g/l of L-lysine in a suitable medium under suitable conditions.

In a fermentative process according to the invention, a *Corynebacterium glutamicum* modified in accordance with the present invention and having the ability to excrete L-lysine is cultivated in a suitable medium under suitable conditions. Due to the ability to excrete L-lysine the concentration of the L-lysine increases and accumulates in the medium during the fermentative process and L-lysine is thus produced.

A suitable medium used for the production of L-lysine by a fermentative process contains a carbon source, a nitrogen source, a phosphorus source, inorganic ions and other organic compounds as required.

Suitable carbon sources include glucose, fructose, sucrose as well as the corresponding raw materials like starch hydrolysate, molasses or high fructose corn syrup.

As nitrogen source organic nitrogen-containing compounds such as peptones, meat extract, soybean hydrolysates or urea, or inorganic compounds such as ammonium sulphate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used.

Inorganic ions like potassium, sodium, magnesium, calcium, iron and further trace elements etc. are supplied as salts of sulfuric acid, phosphoric acid or hydrochloric acid.

Other organic compounds mean essential growth factors like vitamins e.g. thiamine or biotin or L-amino acids e.g. L-homoserine.

The media components may be added to the culture in form of a single batch or be fed in during the cultivation in a suitable manner.

During the fermentative process, the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of 6.0 to 8.5, preferably 6.5 to 8.0. To control foaming, it is possible to employ antifoam agents such as, for example, fatty acid polyalycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the L-lysine sufficient for being recovered has been formed. The cultivation is then completed. This aim is normally achieved within 10 hours to 160 hours. In continuous processes, longer cultivation times are possible.

Thus, the fermentative process results in a fermentation broth which contains the desired L-lysine.

A product containing the L-lysine is then recovered or manufactured in liquid or solid from the fermentation broth. A "fermentation broth" means a medium in which a *Corynebacterium glutamicum* described in the invention has been cultivated for a certain time and under certain conditions.

When the fermentative process is completed, the resulting fermentation broth accordingly comprises:

a) the biomass (cell mass) of the *Corynebacterium glutamicum* of the invention, said biomass having been produced due to propagation of the cells of said *Corynebacterium glutamicum*, b) the desired L-lysine accumulated during the fermentative process, c) the organic by-products accumulated during the fermentative process, and d) the components of the medium employed which have not been consumed in the fermentative process.

The organic by-products include compounds, which may be formed by the *Corynebacterium glutamicum* of the invention during the fermentative process in addition to the production of the L-lysine.

The fermentation broth is removed from the culture vessel or fermentation tank, collected where appropriate, and used for providing a product containing the L-lysine, in liquid or solid form. The expression "recovering the L-lysine-containing product" is also used for this. In the simplest case, the L-lysine-containing fermentation broth itself, which has been removed from the fermentation tank, constitutes the recovered product.

The fermentation broth can subsequently e subjected to one or more of the following process steps:

a) partial (>0% to <80%) to complete (100%) or virtually complete (≥80%, ≥90%, ≥95%, ≥96%, ≥97%, ≥98%, ≥99%) removal of the water, b) partial (>0% to <80%) to complete (100%) or virtually complete (≥80%, ≥90%. ≥95%, ≥96%, ≥97%, ≥98%, ≥99%) removal of the biomass, the latter being optionally inactivated before removal, c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed during the fermentative process, and d) partial (>0% to <80%) to complete (100%) or virtually complete (≥80%, ≥90%, ≥95%, ≥96%, ≥97%, ≥98%, ≥99%, ≥99.3%, ≥99.7%) removal of the residual components of the medium employed or of the residual input materials respectively, which have not been consumed in the fermentative process.

Removal of water (measure a)) can be achieved inter alia by evaporation, using e.g. a falling film evaporator, by reverse osmosis or nanofiltration. The concentrates thus obtained can be further worked up by spray drying or spray granulation. It is likewise possible to dry the fermentation broth directly using spray drying or spray granulation.

Accordingly, a method according to the invention comprises extracting or substantially eliminating water from said fermentation broth. In particular at least 40% (w/w), preferred at least 90% (w/w), more preferred at least 95% (w/w) water are extracted from the fermentation broth.

Removal of the biomass (measure b)) can be achieved inter alia by centrifugation, filtration or decantation or a combination thereof.

Removal of the organic by-products (measure c) or removal of residual components of the medium (measure d) can be achieved inter alia by chromatography, e.g. ion exchange chromatography, treatment with activated carbon or crystallization. In case the organic by-products or residual components of the medium are present in the fermentation broth as solids they can be removed by measure b).

Accordingly, the manufacturing of an L-lysine product according to the invention may further comprise a purification step, preferably selected from the group consisting ion exchange chromatography, treatment with activated carbon or crystallization.

Thus, e.g. a product containing L-lysine×HCl, preferably containing ≥80% L-lysine×HCl, particularly preferred ≥90% L-Iysine×HCl or ≥95% L-lysine×HCl can be obtained.

Thus, a concentration or purification of the L-lysine is achieved and a product having the desired content of said L-lysine is provided.

Analysis of L-lysine to determine its concentration at one or more time(s) during the fermentation can take place by separating the L-lysine by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence). A review regarding amino acid analysis can be found inter alia in the textbook "Bioanalytik" by Lottspeich and Zorhas (Spektrum Akademischer Verlag, Heidelberg, Germany 1998).

EXPERIMENTAL SECTION

A) MATERIALS and METHODS

The molecular biology kits, primers and chemicals used and some details of the methods applied are briefly described herewith.

1. Antibiotics and chemicals a. Kanamycin: Kanamycin solution from Streptomyces kanamyceticus from Sigma Aldrich (St. Louis, USA, Cat. no. K0254).

a. Nalidixic acid: Nalidixic acid sodium salt from Sigma Aldrich (St. Louis, USA, Cat. no. N4382).

b. If not stated otherwise, all chemicals were purchased analytically pure from Merck (Darmstadt, Germany), Sigma Aldrich (St. Louis, USA) or Carl-Roth (Karlsruhe, Germany).

2, Cultivation

If not stated otherwise, all cultivation/incubation procedures were performed as follows herewith:

c. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 37° C. and 200 rpm.

d. LB agar (MILLER) from Merck (Darmstadt, Germany Cat. no. 110283) was used for cultivation of *E. coli* strains on agar plates. The agar plates were incubated at 37° C. in an INCU-Line® mini incubator from VWR (Radnor, USA).

e. Brain heart infusion broth (BMI) from Merck (Darmstadt, Germany; Cat, no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 33° C. and 200 rpm.

f. Brain heart agar (BHI-agar) from Merck (Darmstadt, Germany; Cat. no. 11382.5) was used for cultivation of *C. glutamicum* strains on agar plates. The agar plates were incubated at 33° C. in an incubator from Heraeus Instruments with Kelvitron® temperature controller (Hanau, Germany).

3. Determining optical density a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 660 nm (OD660) with the GENios™ plate reader from Teem Group AG (Mannedorf, Switzerland).

4. Centrifugation a. Benchtop centrifuge for reaction tubes with a volume up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13.000 rpm).

b. Benchtop centrifuge for tubes with a volume up to 50 ml Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min, at 4.000 rpm.

5. Detection of mutations using FRET

The presence of a given mutation, e.g. a nucleobase exchange, was detected by real-time PCR in combination with FRET hybridization probes. The term FRET is the abbreviation for fluorescence resonance energy transfer. As real-time PCR instrument a Lightcycler from Roche Diagnostics® was used (see below).

This method was e.g. used by M. J. Lay and C. T. Wittwer (Clinical Chemistry 42 (12), 2262-2267 (1997)) for the genotyping of factor V Leiden. Cyril DS Mamotte (The Clinical Biochemist Reviews 27, 63-75 (2006)) reviews the genotyping of single nucleotide substitutions using this method. Summaries concerning this method may be found in the textbooks Lewin's Genes XII by Jocelyn E. Krebs, Elliott S. Goldstein and Stephan T. Kilpatrick (Jones and Bartlett Publishers, US, 2018), Molecular Diagnostics, 12 Tests that changed everything by W. Edward Highsmith (Humana Press, Springer, N.Y., 2014) or elsewhere in the art.

The FRET hybridization donor probe was labelled with the fluorescent dye fluorescein and the acceptor probe with the fluorescent dye LC-Red640. In essence, the detection method comprised three steps: colony PCR, probe hybridization and subsequent melting curve analysis. The method is simply referred to as real-time PCR herewith.

a. Primers and Probes

The oligonucleotides used were synthesized by eurofins genomics GmbH (Ehersberg, Germany).

b. Template

As PCR template the total DNA contained in a colony was used. It was prepared by taking cell material with a toothpick from a colony on an agar plate and placing the cell material directly into the PCR reaction tube. The cell material was heated for 10 sec. with 800 W in a microwave oven type Mikrowave & Grill from SEVERIN Elektrogerate GmbH (Sundem, Germany) and then the PCR reagents were added to the template in the PCR reaction tube.

b. Reaction Mix

The Type-It® Fast SNP probe PCR Kit (Type-it Kit) from Qiagen (Hilden, Germany, Cat. No. 206045) was used for real-time detection of the mutations. Therefore 2.5 µl of the Qiagen Fast SNP Puffer (2×) was mixed with 0.5 µl of each of the LC-PCR-Primers [10 µM] and 0.5 µl of each of the 1:500 diluted acceptor and donor probe [100 pmol/µl] to get the mastermix for the real-time PCR.

TABLE 1

Thermocycling conditions for PCR with the LightCycler® (step 1-3) and melting curve analysis (step 4-6).
PCR-program

| Step | Time [sec.] | T [° C.] | Description |
|---|---|---|---|
| 1 | 15 | 95 | Denaturation step (and Activation of HotStarTaq ™ DNA polymerase) |
| 2 | 05 | 55 | Annealing step |
| 3 | 30 | 72 | Elongation step Repeat step 1 to 3: 50 x |
| 4 | 10 | 95 | Denaturation step |
| 5 | 30 | 40 | Probe hybridisation |
| 6 | | 40-80 | Melting curve analysis |
| 7 | | 80-40 | Cooling | c. PCR Cycler

The reactions were carried out in a LightCycler® 2.0 Instrument and analysed with LightCycler® Software 4.1 of Roche Diagnostics (Rotkreuz, Switzerland).

6. Chemical transformation of *E. coli*

*E. coli* K-12 strain S17-1 was used as donor for conjugational transfer of plasmids based on pK18mobsacB from *E. coli* to *C. glutamicum*. Strain S17-1 is described by Simon, R. et al. (Bio/Technology 1, 784-794, 1983). It is available from the American Type Culture Collection under the access number ATCC47055.

Chemically competent E. coli S17-1 cells were made as follows: A preculture of 10 ml LB medium (10 ml liquid medium per 100 ml Erlenmeyer flask with 3 baffles) was inoculated with 100 µl bacterial suspension of strain 517-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM $CaCl_2$ solution and incubated on ice for 30 min. After another centrifugation step, the pellet was resuspended in 5 ml ice-cold 50 trim $CaCl_2$ solution and the suspension incubated on ice for 30 min. The cell suspension was then adjusted to a final concentration of 20% glycerol (v/v) with 85% (v/v) sterile ice-cold glycerol. The suspension was divided into 50 µl aliquots and stored at −80° C. To transform S17-1 cells, the protocol according to Tang et al. (Nucleic Acids Res. 22(14), 2857-2858, 1994) with a heat shock of 45 sec. was used.

7. Conjugation of C. glutamicum

The pK18mobsacB plasmid system described by Schäfer et al. (Gene 145, 69 73, 1994) was used to integrate desired DNA fragments into the chromosome of C. glutamicum. A modified conjugation method of Schafer et al. (Journal of Bacteriology 172, 1663 1666, 1990) was used to transfer the respective plasmid into the desired C. glutamicum recipient strain.

Liquid cultures of the C. glutamicum strains were carried out in BHI medium at 33° C. The heat shock was carried out at 48.5° C. for 9 min. Transconjugants were selected by plating the conjugation batch on EM8 agar (Table 2), which was supplemented with 25 mg/l kanamycin and 50 mg/l nalidixic acid. The EM8 agar plates were incubated for 72 h at 33° C.

TABLE 2

Composition of the EM8 agar

| Components | Concentration (g/l) |
| --- | --- |
| Glucose (sterile-filtered) | 23 |
| CSL (corn steep liquor; Roquette; solid content 48 ± 2% w/w) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7 H_2O$ | 0.5 |
| $FeSO_4 \cdot 7 H_2O$ | 0.01 |
| $CuSO_4 \cdot 5 H_2O$ | 0.001 |
| $ZnSO_4 \cdot 7 H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. An aliquot was taken from the liquid culture suitably diluted and plated (typically 100 to 200 µl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined for integration of the desired DNA fragment by means of real-time PCR.

8. Glycerol stocks of E. coli and C. glutamicum strains

For long time storage of E. coli and C. glutamicum strains glycerol stocks were prepared. Selected E. coli clones were cultivated in 10 ml LB medium supplemented with 2 g/l glucose. Selected C. glutamicum clones were cultivated in twofold concentrated BHI medium supplemented with 2 g/l glucose. Cultures of plasmid containing E. coli strains were supplemented with 50 mg/l kanamycin. Cultures of plasmid containing C. glutamicum strains were supplemented with 25 mg/l kanamycin. The medium was contained in 100 ml Erlenmeyer flasks with 3 baffles. It was inoculated with a loop of cells taken from a colony and the culture incubated for about 18 h at 37° C. and 200 rpm in the case of E. coli and 33° C. and 200 rpm in the case of C. glutamicum. After said incubation period 1.2 ml 85% (v/v) sterile glycerol were added to the culture. The obtained glycerol containing cell suspension was then aliquoted in 2 ml portions and stored at −80° C.

9. Cultivation system according to Wouter Duetz (WDS)

The millilitre-scale cultivation system according to Duetz (Trends Microbiol. 2007; 15(10):469-75) was used to investigate the performance of the C. glutamicum strains constructed. For this purpose, 24-deepwell microplates (24 well WDS plates) from Enzy Screen BV (Heemstede, Netherlands; Cat. no. CR1424), filled with 2.5 mL medium were used.

Precultures of the strains were done in 10 ml twofold concentrated BHI medium. The medium was contained in a 100 ml Erlenmeyer flask with 3 baffles. It was inoculated with 100 µl of a glycerol stock culture and the culture incubated for 24 h at 33° C. and 200 rpm. After said incubation period the optical densities OD600 of the precultures were determined.

The main cultures were done by inoculating the 2.5 ml medium containing wells of the 24 Well WDS-Plate with an aliquot of the preculture to give an optical density OD600 of 0.1. As medium for the main culture CGXII medium described by Keilhauer et al. (J. Bacteria 1993 September; 175(17): 5595-5603) was used. For convenience the composition of the CGXII medium is shown in table 3.

TABLE 3

Composition of Keilhauer's CGXII medium.

| Components | Concentration (g/l) |
| --- | --- |
| MOPS (3-(N-Morpholino)propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7 H_2O$ | 0.25 |
| $CaCl_2$ | 0.01 |

TABLE 3-continued

Composition of Keilhauer's CGXII medium.

| Components | Concentration (g/l) |
|---|---|
| $FeSO_4 \cdot 7\ H_2O$ | 0.01 |
| $MnSO_4\ H_2O$ | 0.01 |
| $ZnSO_4 \cdot 7\ H_2O$ | 0.001 |
| $CuSO_4 \cdot 5\ H_2O$ | 0.0002 |
| $NiCl_2\ 6\ H_2O$ | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analysed with the blood glucose-meter OneTouch Vita® from LifeScan (Johnson & Johnson Medical GmbH, Neuss, Germany). After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analysed in the supernatant.

10. Amino acid analyser

The concentration of L-lysine and other L-amino acids in the culture supernatants was determined by ion exchange chromatography using a SYKAM 5433 amino acid analyser from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 1 263 g trisodium citrate, 120 g citric acid, 1100 ml methanol, 100 ml 37% HCl and 2 ml octanoic acid (final pH 3.5) was used. As buffer B an aqueous solution containing in 20 1 392 g trisodium citrate, 100 g boric acid and 2 ml octanoic acid (final pH 10.2) was used. The free amino acids were coloured with ninhydrin through post-column derivatizanon and detected photometrically at 570 nm.

11. Glucose determination with continuous flow system (CFS)

A SANplus multi-channel continuous flow analyser from SKALAR analytic GmbH (Erkelenz, Germany) was used to determine the concentration of glucose in the supernatant. Glucose was detected with a coupled-enzyme assay (Hexokinase/Glucose-6-Phosphate-Dehydrogenase) via NADH formation.

B) EXPERIMENTAL RESULTS

Example 1

Sequence of the NCgl2816 gene of *C. glutamicum* strain DM1933

Strain DM1933 is an L-lysine producer described by Blombach et al. (Applied and Environmental Microbiology 75(2), 419-427, 2009). It is deposited according to the Budapest treaty at the DSMZ under accession number DSM25442. The nucleotide sequence of the chromosome of strain DM1933 was determined by Illumina whole-genome sequencing technology (Illumina Inc., San Diego, Calif., US). It was found that the nucleotide sequence of the NCgl2816 coding sequence of strain DM1933 including the nucleotide sequence upstream and downstream thereof is identical to that of ATCC13032 shown in SEQ ID NO:1. DM1933 contains in its chromosome a variant of the aspartokinase gene encoding a feedback resistant aspartokinase polypeptide. Said feedback resistant aspartokinase polypeptide has the amino acid sequence of SEQ ID NO:6 of the sequence listing, wherein the amino acid threonine (Thr) at position 311 of the amino acid sequence is replaced by isoleucine (Ile). In U.S. Pat. No. 7,338,790 the abbreviation "lysC T3111" is used to indicate said exchange. Blombach et al. use the abbreviation "lysC(T311)".

Example 2

Construction of plasmid pK18mobsacB_NCgl2816_F220C

Plasmid pK18mobsacB_NCgl2816_F220C was constructed to enable incorporation of the mutation causing the amino acid exchange F220C into the nucleotide sequence of the NCgl2816 coding sequence of strain DM1933. The plasmid is based on the mobilizable vector pK18mobsacB described by Schäfer et al. (Gene 145, 69-73, 1994). For the construction of pK18mobsacB_NCgl2816_F220C the NCgl2816_F220C sequence according to SEQ ID NO:7 was synthetized and subcloned into pK18mobsacB by GeneArt (ThermoFisher Scientific (Waltham, USA)).

To assemble the plasmid pk18mobsacB_NCgl2816_F220C the two polynucleotides i.e. the vector pK18mobsacB cut with)(bar and the synthetized and with XbaI digested polynucleotide NCgl2816_F220C were ligated and transformed in *E. coli* by GeneArt (ThermoFisher Scientific (Waltham, USA)).

Example 3

Construction of strain DM1933NCgl2816_F220C

The plasmid pK18mobsacB_NCgl2816_F220C obtained in example 2 was used to incorporate the mutation leading to the amino acid exchange F220C (see nucleotide position 810 of SEQ ID NO:7) into the chromosome of the L-lysine producer DM1933. Chemically competent cells of *E. coli* strain S17-1 were transformed with plasmid DNA of pK18mobsacB_NCgl2816_F220C. The modified conjugation method of Schäfer et al. (Journal of Bacteriology 172, 1663 1666, 1990) as described in materials and methods was used for conjugal transfer into the strain DM1933 and for selection of transconjugant clones by virtue of their saccharose resistance and kanamycin sensitivity phenotype. Transconjugant clones were analyzed by real-time PCR using the Type-it Kit and the primers LC-NCgl2818_1 and LC-NCgl2816_220 for PCR amplification and NCgl2816_220_C as acceptor probe and NCgl2816_220_A as donor probe for melting curve analysis (table 4). Said primers and probes are also listed under SEQ ID NO's 9 to 12 of the sequence listing.

TABLE 4

List of primers and probes used for real-time PCR.

| name | sequence |
|---|---|
| LC-NCgl2818_1 | CTTGCAGCTGGCGTGATCTC |
| LC-NCgl2816_2 | TGGTTGCGTAAGCAACGATG |

TABLE 4-continued

List of primers and probes used for real-time PCR.

| name | sequence |
|---|---|
| NCgl2816_220_C[1] | GATACGCTTGCACTCGGGGG |
| NCgl2816_220_A[2] | CCTTCAGAGGCATCTTTACCTGCTGGCCGGA |

[1]acceptor probe labelled with LC-Red640 at the 5'-end and phosphorylated at the 3'-end
[2]donor probe labelled with fluorescein at the 3'-end One of the transconjugant clones thus characterized was called DM1933_NCgl2816_F220C. A glycerol stock culture of the transconjugant clone was prepared and used as starting material for further investigations.

Thus, the NCgl2816 gene of strain DM1933 was mutated with the effect that the amino acid phenylalanine at position 220 of the amino acid sequence of the encoded NCgl2816 polypeptide was replaced by cysteine.

Example 4

L-lysine production by strain DM1933_NCgl2816_F220C

Strains DM1933 (reference) and DM1933_NCgl2816_F220C obtained in example 3 were analyzed for their ability to produce L-lysine from glucose by batch cultivation using the cultivation system according to Wouter Duetz.

As medium CGXII containing 20 g/l glucose as carbon source was used. The cultures were incubated for 45 h until complete consumption of glucose as confirmed by glucose analysis using blood glucose-meter and the concentrations of L-lysine and the optical density OD660 were determined. The result of the experiment is presented in table 5.

TABLE 5

L-lysine production by strain DM1933_NCgl2816_F220C.

| strain | L-lysine[1] (g/l) | OD660 |
|---|---|---|
| DM1933 | 3.7 | 9.5 |
| DM1933_NCgl2816_F220C | 4.0 | 9.0 |

[1]as L-lysine × HCl

The experiment shows that L-lysine production was increased in strain DM1933_NCgl2816_F220C as compared to the parent strain DM1933.

The invention claimed is:

1. A method for the fermentative production of L-lysine, comprising:
   a) providing a bacterium of the species *Corynebacterium glutamicum* having an ability to excrete L-lysine containing in the bacterium's chromosome a polynucleotide encoding a polypeptide comprising an amino acid sequence of SEQ ID NO:2, wherein an amino acid phenylalanine at position 220 of the amino acid sequence of SEQ ID NO:2 is substituted by a different proteinogenic amino acid,
   b) cultivating the bacterium in a suitable medium under suitable conditions, and
   c) accumulating said L-lysine in the medium to form an L-lysine containing fermentation broth.

2. The method of claim 1, wherein, in the bacterium, the amino acid at position 220 of the amino acid sequence of SEQ ID NO:2 is cysteine.

3. The method of claim 2, wherein, in the bacterium, the polynucleotide encoding said amino acid sequence comprises a nucleotide sequence of positions 343 to 1641 of SEQ ID NO:1 with nucleotides at positions 1000 to 1002 being tgt or tgc.

4. The method of claim 3, wherein the nucleotides at positions 1000 to 1002 are tgc.

5. The method of claim 2, wherein, in the bacterium, the polynucleotide encoding said amino acid sequence comprises a nucleotide sequence of positions 343 to 1644 of SEQ ID NO:1 with nucleotides at positions 1000 to 1002 being tgt or tgc.

6. The method of claim 5, wherein the nucleotides at positions 1000 to 1002 are tgc.

7. The method of claim 2, wherein, in the bacterium, the polynucleotide encoding said amino acid sequence comprises a nucleotide sequence of positions 221 to 1644 of SEQ ID NO:1 with nucleotides at positions 1000 to 1002 being tgt or tgc.

8. The method of claim 7, wherein the nucleotides at positions 1000 to 1002 are tgc.

9. The method as claimed in claim 1, further comprising manufacturing of an L-lysine containing product from the L-lysine containing fermentation broth.

10. The method as claimed in claim 1, further comprising extracting or substantially eliminating water from the L-lysine containing fermentation broth.

11. The method of claim 9, wherein said manufacturing comprises purification.

* * * * *